US010905345B2

(12) United States Patent
Gupta et al.

(10) Patent No.: US 10,905,345 B2
(45) Date of Patent: Feb. 2, 2021

(54) NON-INVASIVE METHOD AND SYSTEM FOR CHARACTERIZING CARDIOVASCULAR SYSTEMS

(71) Applicant: Analytics For Life Inc., Toronto (CA)

(72) Inventors: Sunny Gupta, East York (CA); Mohsen Najafi Yazdi, Kingston (CA); Timothy William Fawcett Burton, Ottawa (CA); Shyamlal Ramchandani, Kingston (CA); Derek Vincent Exner, Calgary (CA)

(73) Assignee: Analytics for Life Inc., Toronto (CA)

( * ) Notice: Subject to any disclaimer, the term of this patent is extended or adjusted under 35 U.S.C. 154(b) by 20 days.

(21) Appl. No.: 16/274,803

(22) Filed: Feb. 13, 2019

(65) Prior Publication Data
US 2019/0313926 A1    Oct. 17, 2019

Related U.S. Application Data

(63) Continuation of application No. 15/961,213, filed on Apr. 24, 2018, now Pat. No. 10,362,951, which is a
(Continued)

(51) Int. Cl.
*A61B 5/0402* (2006.01)
*A61B 5/044* (2006.01)
(Continued)

(52) U.S. Cl.
CPC .......... *A61B 5/0402* (2013.01); *A61B 5/0205* (2013.01); *A61B 5/044* (2013.01);
(Continued)

(58) Field of Classification Search
CPC .................................................. A61B 5/0402
(Continued)

(56) References Cited

U.S. PATENT DOCUMENTS

| 5,029,082 A | 7/1991 | Shen et al. |
|---|---|---|
| 6,325,761 B1 | 12/2001 | Jay |

(Continued)

FOREIGN PATENT DOCUMENTS

WO    2012/106729    8/2012

OTHER PUBLICATIONS

Benmalek, M., et al., "Digital fractional order operators for R-wave detection in electrocardiogram signal," IET Signal Processing, vol. 3, Issue 5, 2009, pp. 381-391.
(Continued)

*Primary Examiner* — Nadia A Mahmood
(74) *Attorney, Agent, or Firm* — Meunier Carlin & Curfman LLC

(57) ABSTRACT

The present disclosure uses physiological data, ECG signals as an example, to evaluate cardiac structure and function in mammals. Two approaches are presented, e.g., a model-based analysis and a space-time analysis. The first method uses a modified Matching Pursuit (MMP) algorithm to find a noiseless model of the ECG data that is sparse and does not assume periodicity of the signal. After the model is derived, various metrics and subspaces are extracted to image and characterize cardiovascular tissues using complex-sub-harmonic-frequencies (CSF) quasi-periodic and other mathematical methods. In the second method, space-time domain is divided into a number of regions, the density of the ECG signal is computed in each region and inputted into a learning algorithm to image and characterize the tissues.

20 Claims, 19 Drawing Sheets

Related U.S. Application Data continuation of application No. 15/588,148, filed on May 5, 2017, now Pat. No. 9,968,275, which is a continuation of application No. 15/061,090, filed on Mar. 4, 2016, now Pat. No. 9,655,536, which is a continuation of application No. 13/970,580, filed on Aug. 19, 2013, now Pat. No. 9,289,150.

(60) Provisional application No. 61/684,217, filed on Aug. 17, 2012.

(51) Int. Cl.
  *A61B 5/0205* (2006.01)
  *A61B 5/04* (2006.01)
  *A61B 5/1455* (2006.01)
  *A61B 5/00* (2006.01)
  *A61B 5/021* (2006.01)

(52) U.S. Cl.
  CPC ...... *A61B 5/04011* (2013.01); *A61B 5/04012* (2013.01); *A61B 5/04017* (2013.01); *A61B 5/14551* (2013.01); *A61B 5/7235* (2013.01); *A61B 5/021* (2013.01); *A61B 2576/023* (2013.01)

(58) Field of Classification Search
  USPC .......................................................... 600/523
  See application file for complete search history.

(56) References Cited

U.S. PATENT DOCUMENTS

| | | |
|---|---|---|
| 6,709,399 B1 | 3/2004 | Shen et al. |
| 9,131,864 B2 | 9/2015 | Korenberg |
| 2002/0156385 A1 | 10/2002 | Feng et al. |
| 2009/0082640 A1 | 3/2009 | Kovach et al. |
| 2009/0312648 A1 | 12/2009 | Zhang et al. |
| 2011/0087121 A1 | 4/2011 | Zhang et al. |
| 2013/0046151 A1 | 2/2013 | Bosul et al. |
| 2014/0309707 A1 | 10/2014 | Marculescu et al. |

OTHER PUBLICATIONS

Exner, D.V., et al., "Noninvasive Risk Assessment Early After a Myocardial Infarction," The REFINE Study, Journal of the American College of Cardiology, vol. 50, No. 24, 2007, pp. 2275-2284.

Mallat, S.G., et al., "Matching Pursuits with Time-Frequency Dictionaries," IEEE Transactions on Signal Processing, vol. 41, No. 12, 1993, pp. 3397-3415.

Yang, H., Bukkapatnam, S. T., & Komanduri, R. (Mar. 2012). Spatiotemporal representation of cardiac vectorcardiogram (VCG) signals. BioMedical Engineering Online, 11, 16.

Adapted from the American Society of Nuclear Cardiology. J Nucl Cardiol.1999;6:G47-G84.

Adapted from the American Society of Nuclear Cardiology. J Nucl Cardiol.1999;6:G47-G84.

Blinded estimation of left ventricular fibrosis by high-resolution ECG vs. cardiac magnetic resonance expressed as percent late gadolinium enhancement (N = 30).

Blinded regional localization of left ventricular abnormality (hypertrophy / fibrosis) by high-resolution ECG vs. cardiac magnetic resonance (N = 30).

Overall agreement 80%
Kappa 0.66; p < 0.0001
(expected agreement 42%)

|  |  | CMR Abnormality | | |
|---|---|---|---|---|
|  |  | None | Septal | Lateral |
| ECG Abnormality | None | 5 | 1 | 0 |
|  | Septal | 1 | 15 | 0 |
|  | Lateral | 1 | 3 | 4 |

*FIG 13*

NON-INVASIVE METHOD AND SYSTEM FOR CHARACTERIZING CARDIOVASCULAR SYSTEMS

CROSS-REFERENCE TO RELATED APPLICATION

This is a continuation application of U.S. application Ser. No. 15/961,213, filed Apr. 24, 2018, now U.S. Pat. No. 10,362,951, which is a continuation application of U.S. patent application Ser. No. 15/588,148, filed May 5, 2017, now issued as U.S. Pat. No. 9,968,275, which is a continuation application of U.S. application Ser. No. 15/061,090, filed Mar. 4, 2016, now issued as U.S. Pat. No. 9,655,536, which is a continuation application of U.S. application Ser. No. 13/970,580, filed Aug. 19, 2013, now U.S. Pat. No. 9,289,150, which claims priority to, and the benefit of, U.S. Provisional Patent Application No. 61/684,217, filed on Aug. 17, 2012, entitled "NON-INVASIVE METHOD AND SYSTEM FOR CHARACTERIZING CARDIOVASCULAR SYSTEMS," each of which is incorporated herein by reference in its entirety.

BACKGROUND

The current algorithms employed in signal processing of electrocardiographic (ECG) signals are rudimentary and have limited diagnostic accuracy. In fact, validated and accepted ECG scoring systems like the Selvester score have only a 71% accuracy in detecting a previous myocardial infarction when compared to cardiac magnetic resonance (CMR) imaging and the ECG is recognized as having significant limitations in ruling in or ruling out an acute myocardial infarction. The ability of the ECG to detect left ventricular hypertrophy and other conditions is also extremely limited. In fact, the ECG not recommended to be used to rule out left ventricular hypertrophy in patients with hypertension. We claim that analysis of ECG data can be improved upon using techniques to identify and quantify phase space changes to localize, image, and characterize architectural features and function of cardiovascular and other mammalian tissues.

There are various time domain and frequency domain signal-processing techniques which are being used for the analysis of physiological signals to obtain more detailed information. While time domain techniques are often used, they alone are incapable of quantifying certain fluctuation characteristics of a number of pathologies related to physiological signals. For example, traditional methods for performing frequency-domain analysis of surface ECG signals, such as the Fourier transform, are limited since they do not address the aperiodic random nature of biological and electromagnetic noise. For example, complex ECG waveforms with large variation in their morphologies have been shown to occur with the development of arrhythmias. Dominant frequency analysis on ECG data can be problematic since non-linear dynamic systems can appear to generate random noise. Discrete fast Fourier transforms and wavelet analysis have been shown experimentally to be incapable of detecting deterministic chaos in the presence of strong periodicity which tends to obscure the underlying non-linear structures.

BRIEF SUMMARY

The present disclosure generally relates to non-invasive methods and techniques for characterizing mammalian cardiovascular systems. More specifically, the present disclosure relates to non-invasive methods that utilize electrocardiographic (ECG) phase space data to localize, image, and characterize architectural features and function of the myocardium and cardiovascular tissues.

The present disclosure uses physiological data, ECG signals as an example, to evaluate cardiac structure and function in mammals. However, it is also claimed that other physiological data can similarly be used to image and characterize other organ systems in mammals using a similar approach. The present disclosure provides an improved and efficient method to image and characterize the heart using a high-resolution ECG data. It is claimed that these ECG data can be used to identify, localize, and characterize cardiovascular tissues. ECG waveforms possess high-dimensional data with complex nonlinear variability that cannot be efficiently captured by traditional modeling techniques. Two approaches, namely model-based analysis and space-time analysis, are used to study the dynamical and geometrical properties of ECG data. The first method uses a modified Matching Pursuit (MMP) algorithm to find a noiseless model of the ECG data that is sparse and does not assume periodicity of the signal. After the model is derived, various metrics and subspaces are extracted to image and characterize cardiovascular tissues using complex-sub-harmonic-frequencies (CSF) quasi-periodic and other mathematical methods. In the second method, space-time domain is divided into a number of regions (12 regions for ventricular tissue, see FIGS. 10A and 10B and 6 regions for atrial tissues); the density of the ECG signal is computed in each region and inputted into a learning algorithm to image and characterize the tissues.

As such, the present disclosure provides for a non-invasive system and method whereby ECG measurements can be taken and transformed to characterize and image architectural features of cardiovascular and other tissues. Further, the present disclosure provides a system and method to image (inverse ECG problem) and localize architectural features and function of cardiovascular tissues.

DESCRIPTION OF THE DRAWINGS

Exemplary embodiments of the present disclosure will hereinafter be described in conjunction with the following drawing figures, wherein like numerals denote like elements, and wherein:

FIG. 13 demonstrates the ability of the disclosed methods to localize alterations in cardiac tissues, in this case hypertrophy/fibrosis, from only a high resolution ECG signal and the methods disclosed. This three-by-three table indicates that the localization by ECG using the methods disclosed is comparable to that of CMR.

DETAILED DESCRIPTION

Figure 1A:
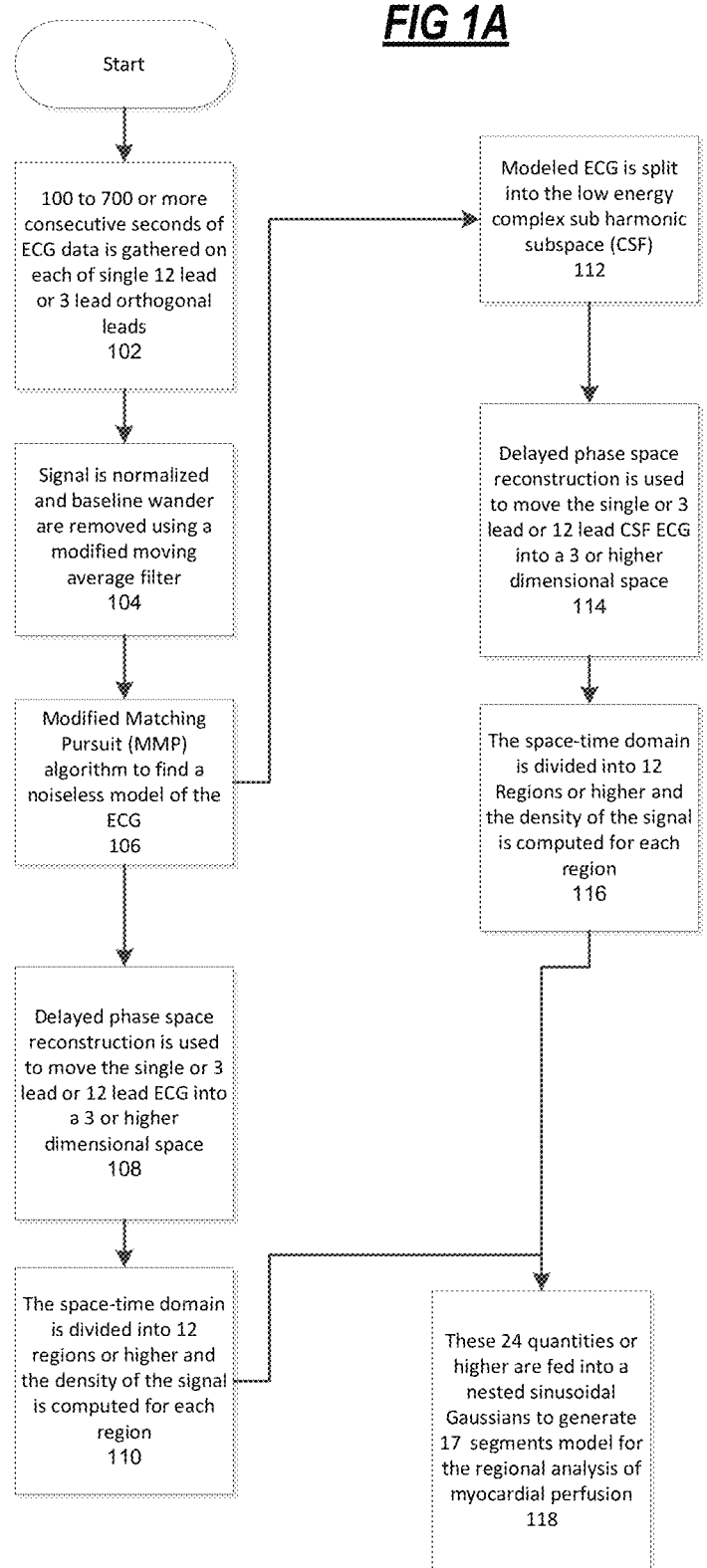
FIGS. 1A and 1B show an overview of processes and algorithms to obtain a phase space representation and to derive a three-dimensional (3-D) model of the heart.
Figure 1B:
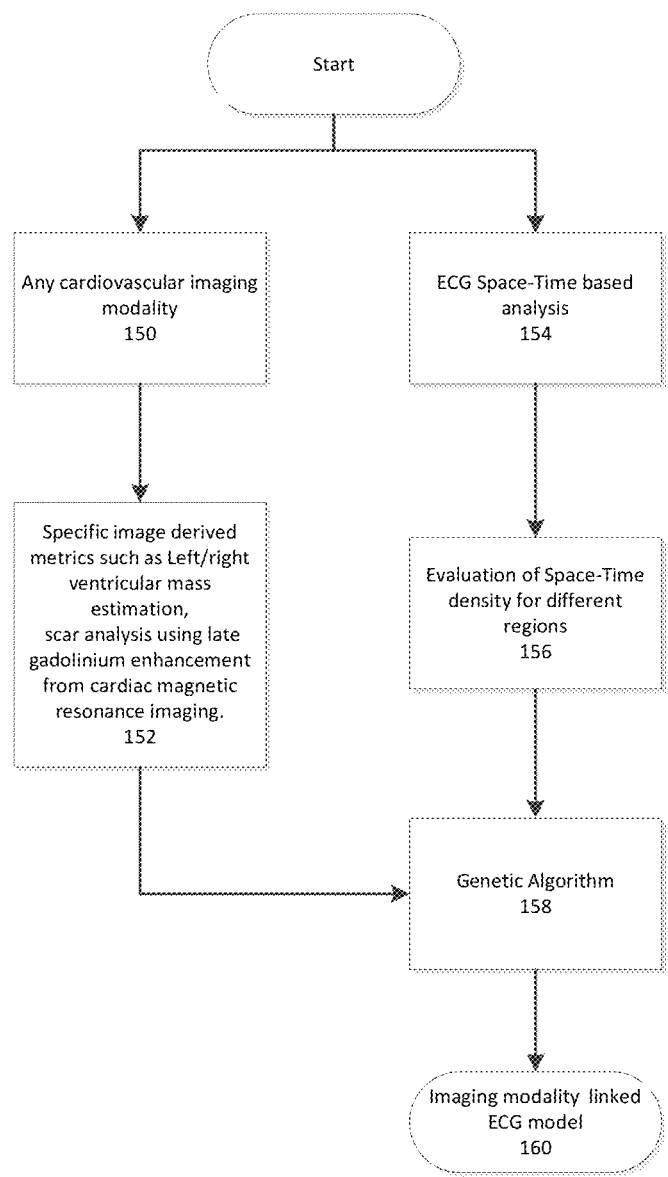

FIGS. 1A and 1B illustrate a high-level overview of the various processes and algorithms implemented by the present disclosure to obtain a phase space representation and to derive a 3-D model of the heart. Referring to FIG. 1A, there is illustrated an operational flow diagram for the regional analysis of myocardial perfusion. At 102, 100 to 700 or more consecutive seconds of ECG data is gathered on each of single 12 lead or 3 lead orthogonal leads. At 104, the signal is normalized and baseline wander are removed using a modified moving average filter. At 106, a Modified Matching Pursuit (MMP) algorithm may be used to find a noiseless model of the ECG data. At 108, delayed phase space reconstruction is used to move the single or 3 lead or 12 lead ECG into a 3 or higher dimensional space. At 110, the space-time domain is divided into 12 regions or higher and the dynamical density of the signal is computed for each region.

Dynamical signal density can be computed using non-Fourier or Fourier n dimensional fractional integral summation across all ECG leads on the derived model over the scan window. Typically the order of fractional integral could be −1.5 or −2.5 or any irrational, complex or real number.

Referring back to 106, the flow also proceeds to 112, where the modeled ECG is split into the low energy complex sub harmonic subspace (CSF). At 114, delayed phase space reconstruction is used to move the single or 3 lead or 12 lead CSF ECG into a 3 or higher dimensional space. At 116, the space-time domain is divided into 12 Regions or higher and the density of the signal is computed for each region. At 118, the outputs of 110 and 116 are use to as 24 quantities (or higher) that are fed into a nested sinusoidal Gaussians to generate 17 segments model for the regional analysis of myocardial perfusion.

Referring to FIG. 1B, there is a process for generating a genetic algorithm. At 150, any cardiovascular imaging modality is input. At 152, specific image derived metrics such as Left/right ventricular mass estimation, scar analysis using late gadolinium enhancement from cardiac magnetic resonance imaging. Alternatively or additionally, at 154, an ECG Space-Time based analysis is input. At 156, an evaluation of Space-Time density for different regions is performed. At 158, the output of 152 and/or 156 may be used to generate a genetic algorithm. At 160, an imaging modality linked ECG model is created.

Aspects of FIGS. 1A and 1B are described in more detail below.

Figure 2:
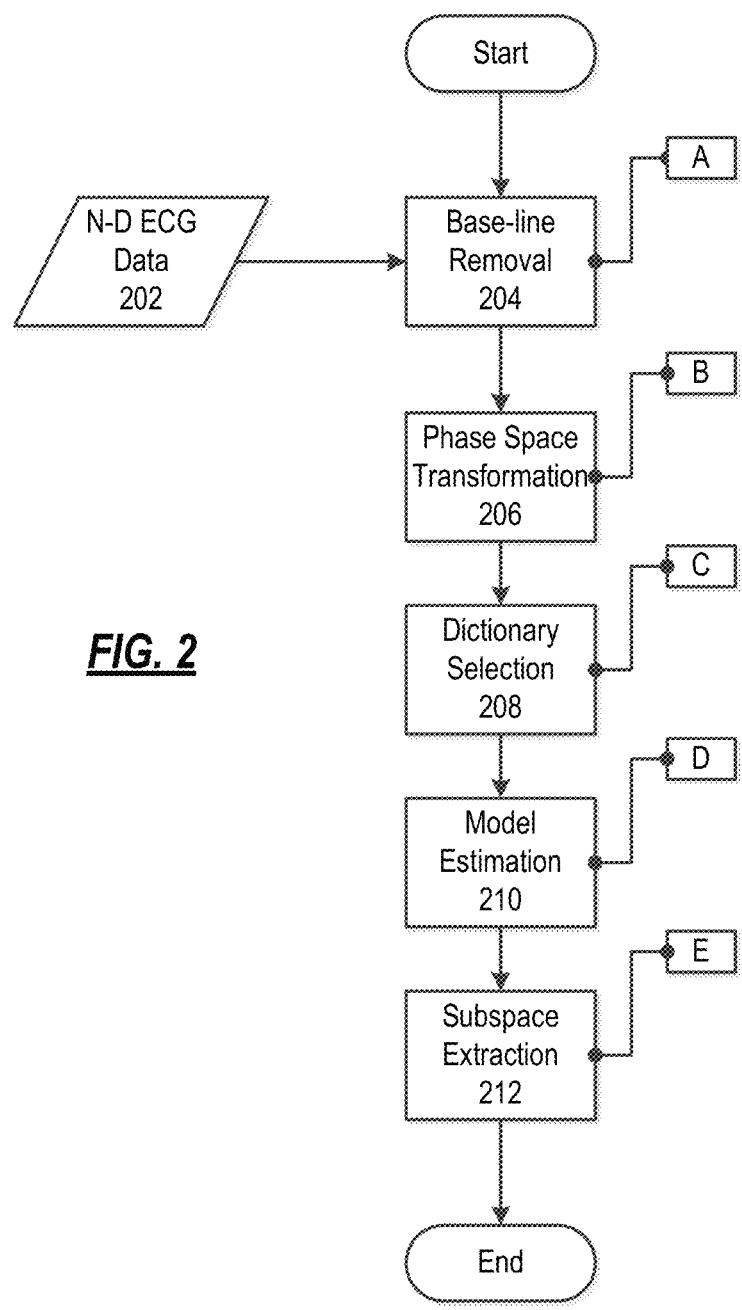
FIG. 2 shows the steps of the model-based analysis to derive a noiseless model from ECG data using an MMP algorithm.

FIG. 2 illustrates the steps of the model-based analysis to derive a noiseless model from ECG data using an MMP algorithm. Step 204 shows the baseline removal step, step 206 represents the phase space transformation step, step 208 presents the dictionary selection step, step 210 illustrates the model estimation step and step 212 demonstrates the subspace extraction step. In FIG. 2, at 202, N-dimensional ECG is input to a modified moving average filter to remove the baseline wander from the data. The output then goes to a phase space transformation process at 206 in which a dynamically rich system (a system that can exhibit many different dynamical behaviors at different values of its parameters) is synchronized with a physiological signal, in this case ECG data, to magnify its dynamical features. For example, Rossler is a good choice as it exhibits various behaviors for different values of its parameters. The defining equations of Rossler system are as follows:

$$\begin{cases} \dot{x} = -y - z \\ \dot{y} = x + ay \\ \dot{z} = b + z(x - c) \end{cases}$$

where a, b, and c are some constants. For fixed values of a=b=0.1, Rossler system exhibits the following behavior for different values of c.

TABLE 1

| Value of c | Dynamical Behavior | Phase Space |
| --- | --- | --- |
| c = 4 | Period-1 Orbit | FIG. 9.A |
| c = 6 | Period-2 Orbit | FIG. 9.B |
| c = 8.5 | Period-4 Orbit | FIG. 9.C |
| c = 8.7 | Period-8 Orbit | FIG. 9.D |
| c = 13 | Sparse Chaos | FIG. 9.E |
| c = 18 | Filled-in Chaos | FIG. 9.F |

Figure 3:
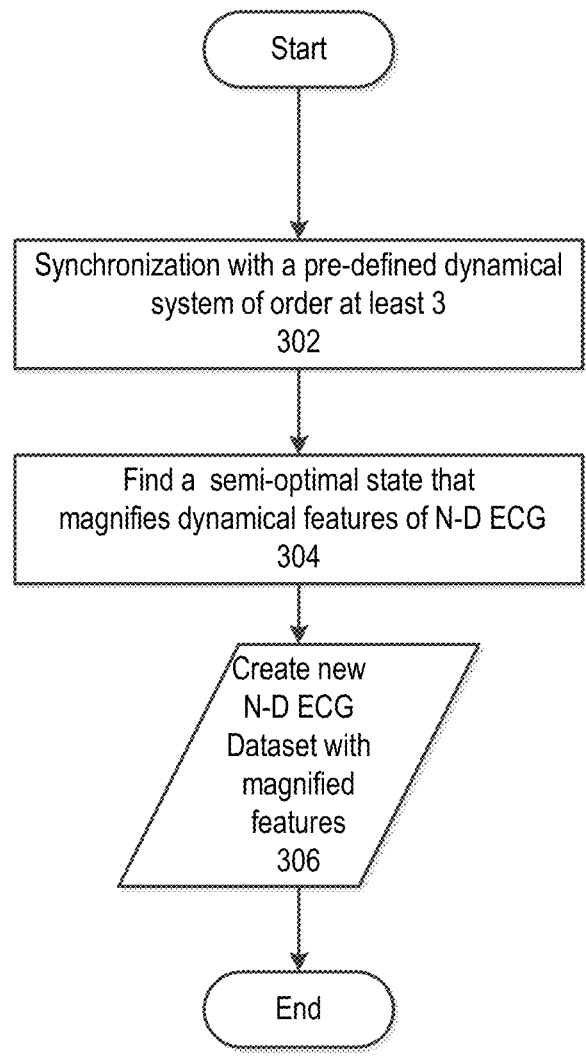
FIG. 3 presents process of phase space transformation.

The ECG data is synchronized with Rossler system and then a semi-optimal state is identified that magnifies dynamical features of the physiological signal under study, FIG. 3.

In accordance with FIG. 3, at 302, the ECG is synchronized with a dynamical system. Next, at 304, a semi-optimal state that magnifies the dynamical features of the ECG is found. This creates a new ECG dataset with magnified features at 306. Synchronization refers to phase space based synchronization of the information of the ECG system to the Rossler system. The subspaces that arise from the differences between the synchronization of these two systems are the magnifications of the dynamical features of the ECG. These subspaces comprise the new ECG dataset.

Referring again to FIG. 2, at 208, the obtained new dataset is then used to find the best dictionary(ies) that can linearly span the input. Each dictionary, $\mathcal{D}$, is a family of waveforms $\mathcal{D} = \{\varphi_i | i \in I\}$ that is used to decompose the input. Various dictionaries are now available such as Wavelet Packets, Cosine Packets, Chirplets, and so on. In accordance with some implementations, complex exponential sinusoids and Time-Frequency are used over complete dictionaries synchronized by a dynamically-rich family of post-transient Rossler trajectories.

Figure 4:
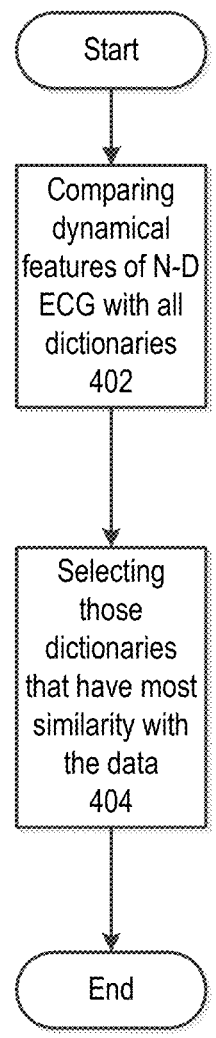
FIG. 4 Illustrates the process of selecting the best dictionaries.

FIG. 4 illustrates the process of selecting the best dictionaries. At 402, different dynamical features, such as Lyapunov exponent and correlation dimension, of the ECG or other physiological signal is compared with a family of different dictionaries. At 404, those dictionaries that have most similarity to the dataset is selected to be used for model estimation, i.e. the member atoms of the selected dictionaries form the set of atoms that will be used in MMP. The dynamical features of the ECG are compared with all the dictionaries and the dictionaries are selected that have the most similarity with the data Referring again to FIG. 2, at 210, the next step is to find a sparse model (extracted from the selected dictionaries) for the physiological signal under study. For example, MMP may be used, which is an iterative process that, at each step, chooses the dictionary atom that best correlates with the signal. This process continues until a pre-defined stopping condition occurs, such as if the number of terms exceeds a threshold and/or the distance of the model and the target in the search space is smaller than a threshold. Finally, the coefficients of the selected atoms are computed.

Figure 5:
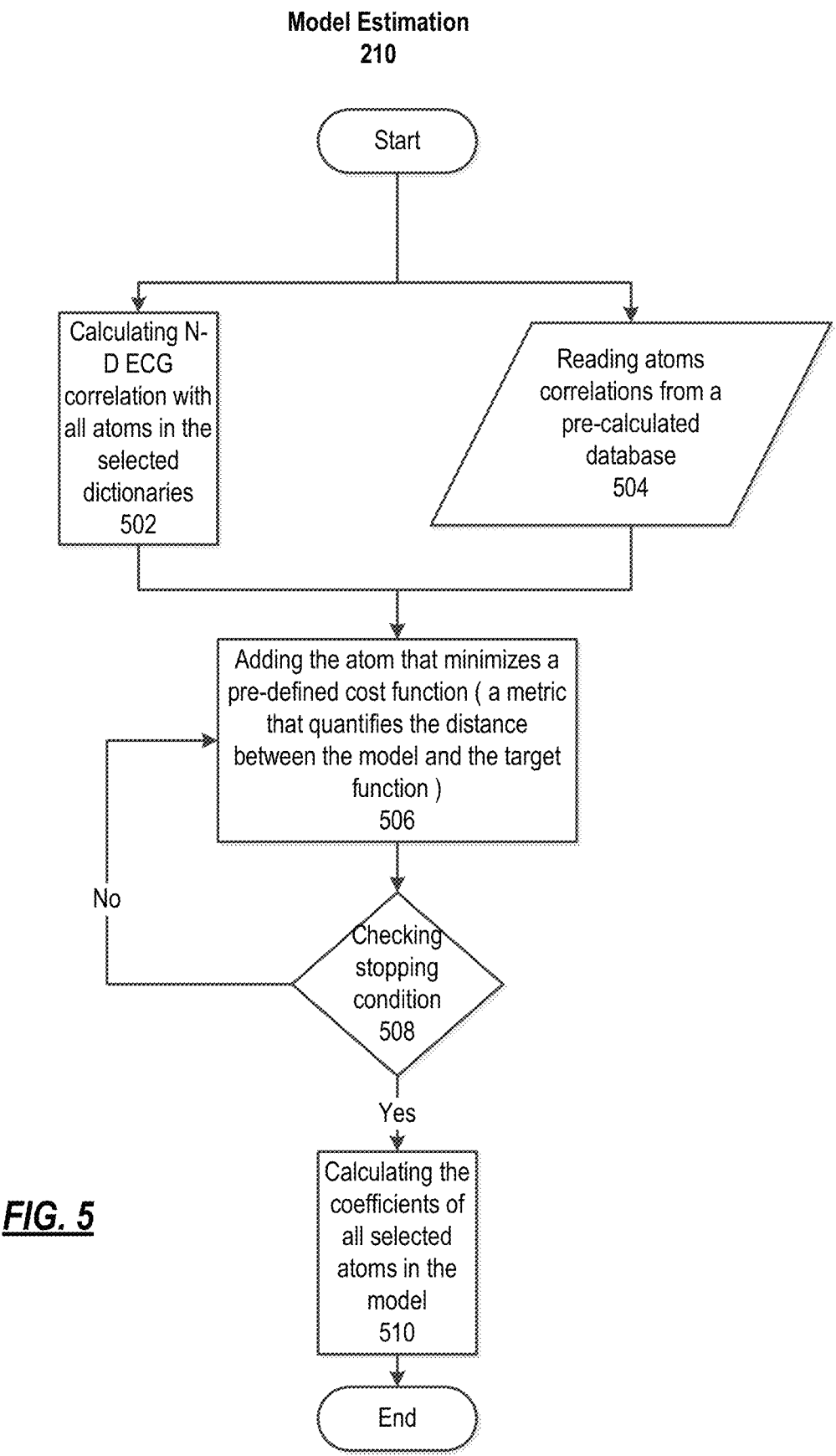
FIG. 5 illustrates model estimation process where sparse linear expansion of selected atoms is used to mimic the ECG signal.

FIG. 5 sketches the process of model estimation using MMP. At 502, the correlation of the ECG dataset with all the atoms in the selected dictionaries is computed. This information, along with the pre-evaluated cross correlation of atoms (504) is used to pick the best atom in each iteration in order to minimize a pre-defined cost function that quantifies a distance in a metric space, such as mean absolute error or mean square error, between the model and the target waveform. After the addition of each atom at 506, a stopping condition is consulted at 508 to determine whether further iterations of the algorithm are necessary. This stopping condition could take into account factors such as the number of atoms already present in the model and the fit of the model against the target waveform. If the stopping condition has been satisfied at 508, the algorithm proceeds to 510 to perform a calculation of the coefficients of the atoms. These coefficients are reclusively calculated using information captured during the iteration of the algorithm in order to optimize the fit of the model against the input waveform. The process begins with reading pre-computed atom correlations and computing the correlations between the input waveform and the atoms. Atoms are iteratively added until the stopping condition is satisfied, at which point the coefficients are calculated Returning to FIG. 2, at 212, different subspaces are extracted from the derived model. Various subspaces, namely CSF trajectory, quasi-periodic and chaotic subspaces, low/high-energy subspace, and fractional derivative of the low/high-energy subspace are extracted from the derived model; however, possible subspaces that could be extracted are not limited to these examples. Each of which represents a dynamical abnormality in the tissue architecture, structure and function.

The last 20% of the selected atoms are used to form a "low energy subspace" signal corresponding to each of the leads. These low energy signals can be called x(t), y(t), and z(t) assuming 3 leads.

There are various time domain and frequency domain signal processing techniques used for the analysis of physiologic signals to obtain more detailed information. CSF exist in many physiological signals, not just the cardiac signals presented, and are likely indicative of other pathophysiological processes not otherwise detectable using prior art methods.

3-D Visualization

Figure 6:
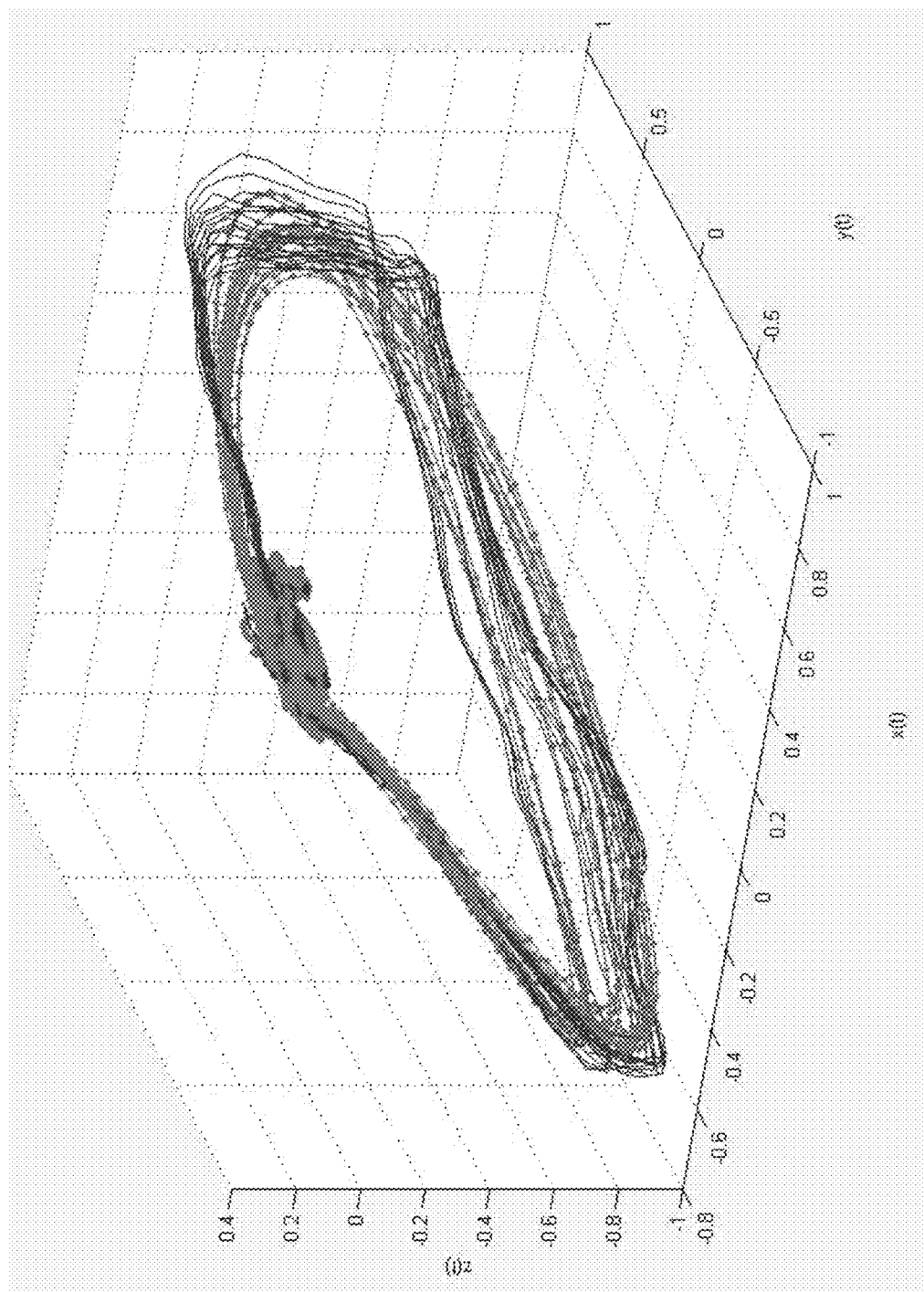
FIG. 6 illustrates one embodiment of a method whereby MMP can be used to generate a 3-D vectorgram, where the blue trajectories are the raw ECG signal plotted in 3 dimensions and red trajectories are the MMP model of the blue.

The output obtained after applying the MMP algorithm on the ECG or other physiological signal, can be represented as a 3-D phase space plot, as shown in FIG. 6. The illustrated 3-D phase space plot illustrates cardiac electrical conduction patterns, and associated alterations in tissue architecture, structure and function. This invention can be used, for example, to detect hypertrophy, ischemia, scar, abnormal electrical channel function (channelopathies) and other forms of inherited or acquired heart disease in mammals. In addition, this method can be used to assess the effects (positive and negative) of various interventions that include medications, toxins, chemotherapeutic agents, surgical procedures, and other interventional procedures such as ablation, pacing, shocks and electrical therapies, and genetic therapies.

Figure 7:
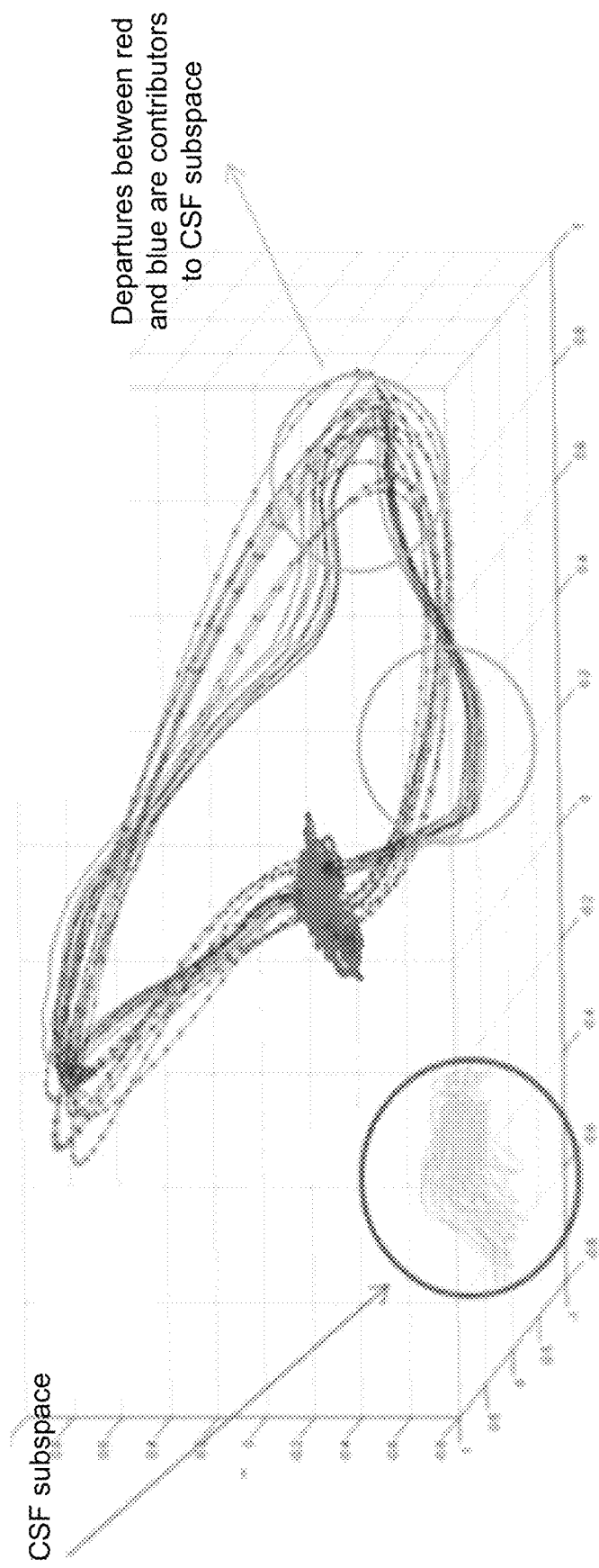
FIG. 7 shows a CSF trajectory derived from an MMP model of the ECG.

The 3-D phase space plot localizes the presence of CSF related to altered tissue. For example, the CSF for the heart can be measured as a time delay and as a 3-D trajectory in the atrial and ventricular sub-spaces. CSF trajectory is associated with those components of the ECG not captured by the dictionary, i.e. there is no linear combination of the atoms of the selected dictionaries that can represent the CSF trajectory. FIG. 7 shows a CSF trajectory derived from an MMP model of an ECG.

Figure 8A:
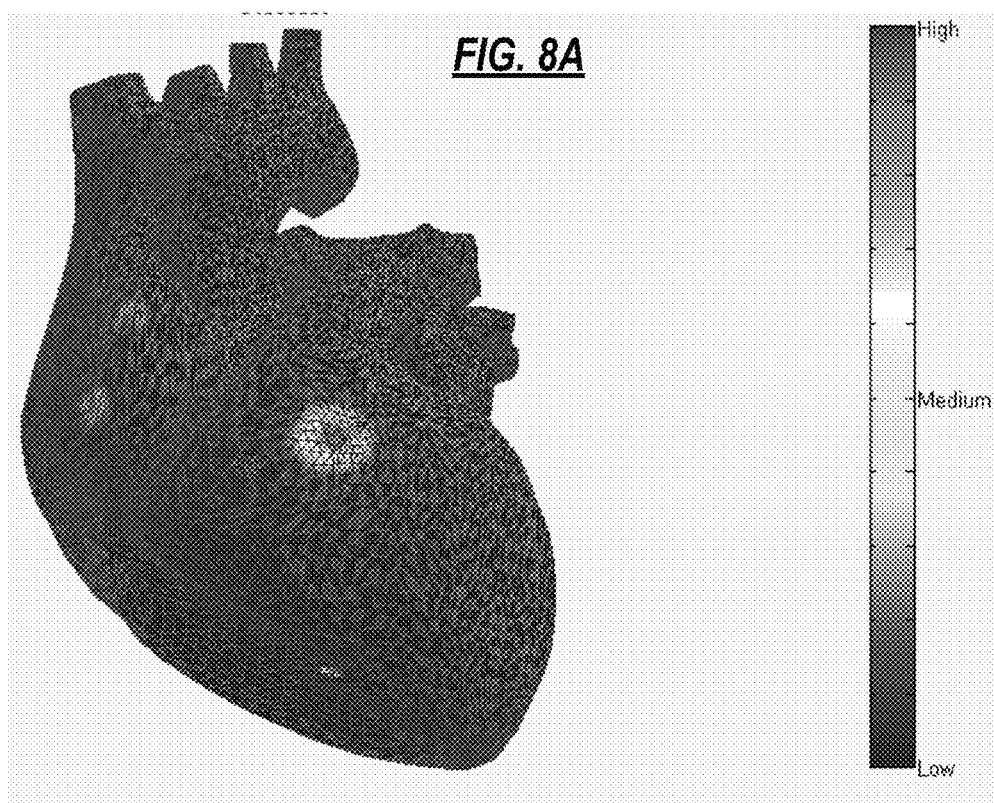
FIG. 8A shows a 3-D model of a heart where abnormal electrical/anatomical features are highlighted in red.
Figure 8B:
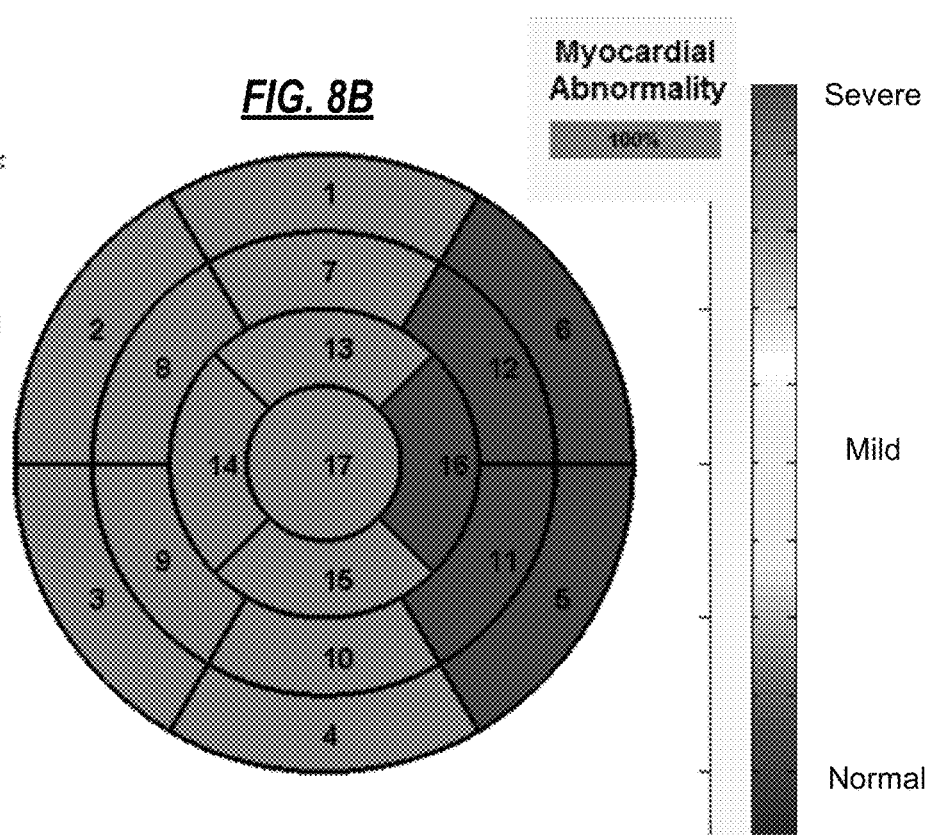
FIG. 8B is the representation of this data using a 17-segment cardiac anatomical map in common use.
Figure 9A:
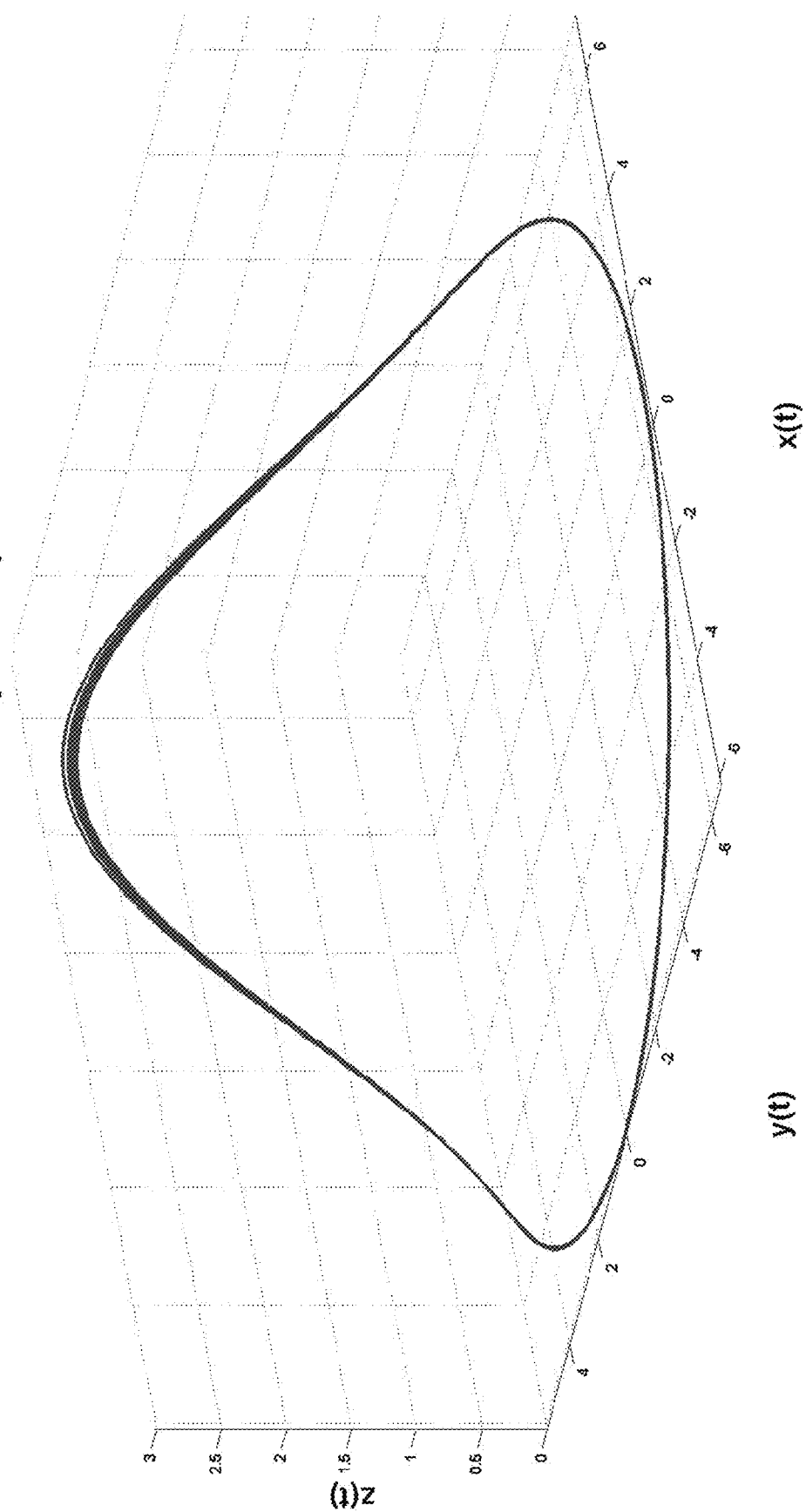
FIGS. 9A-9F present different dynamical behaviors of Rossler system for different values of its parameter, c.
Figure 9B:
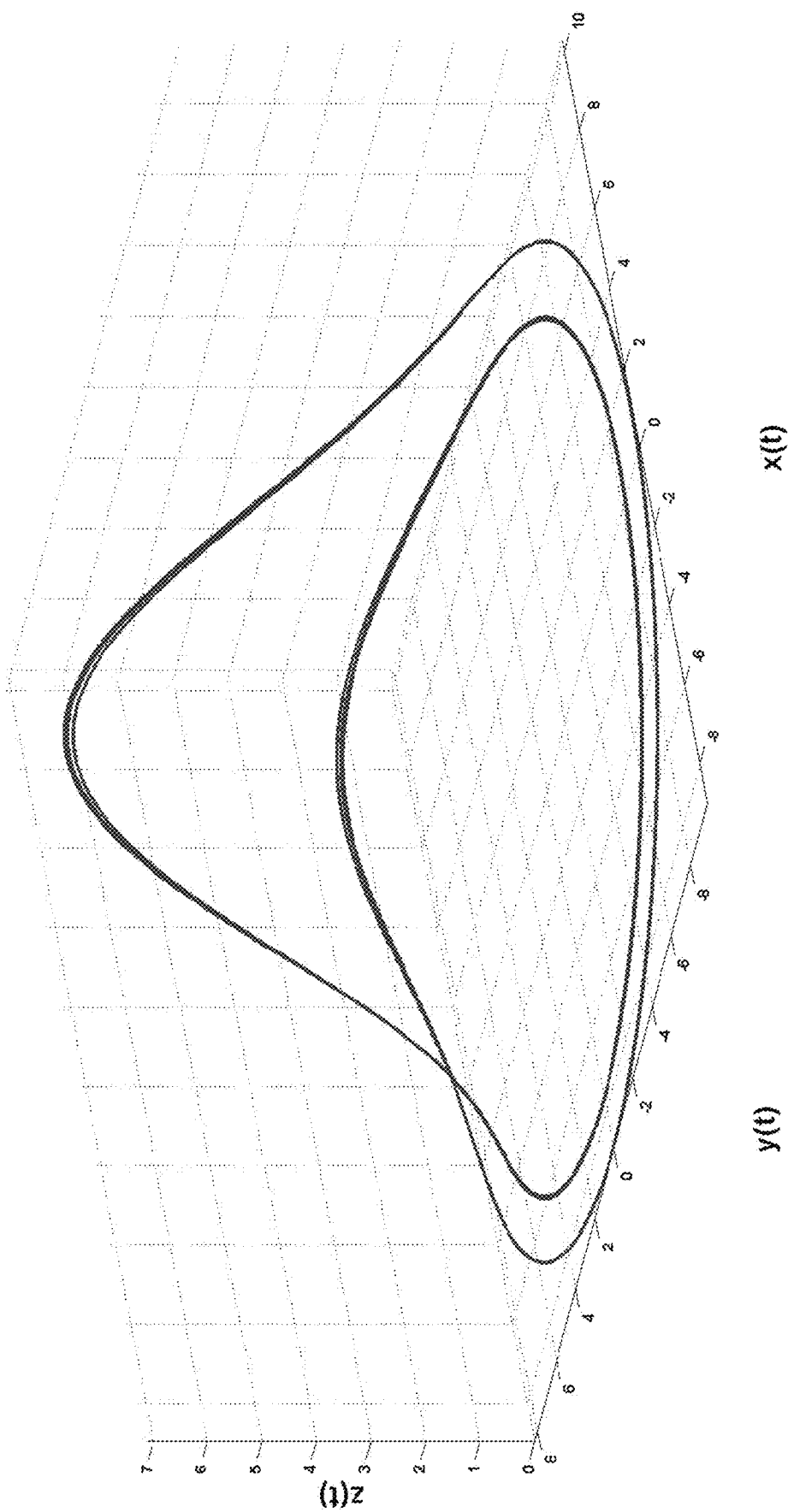
Figure 9C:
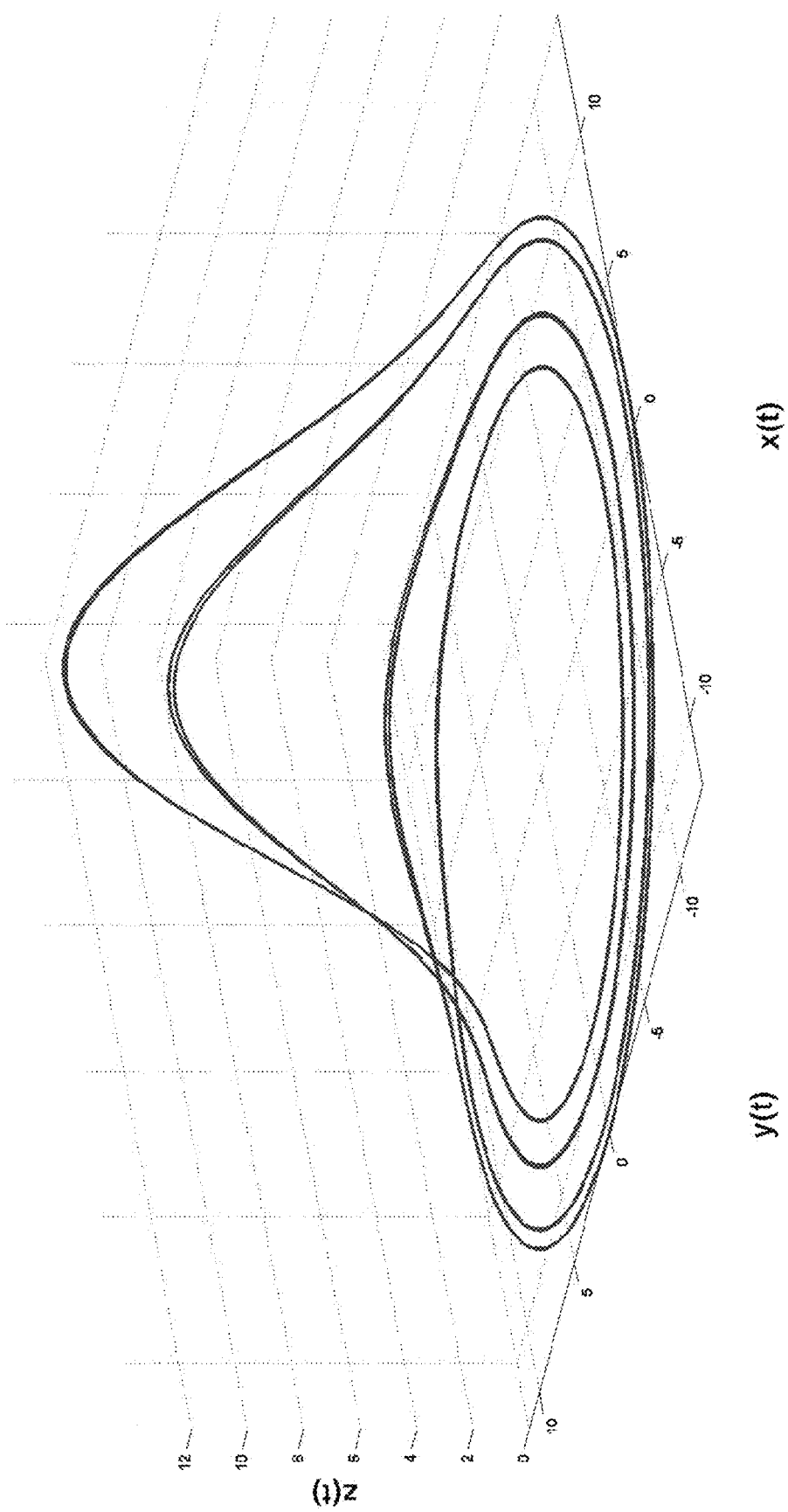
Figure 9D:
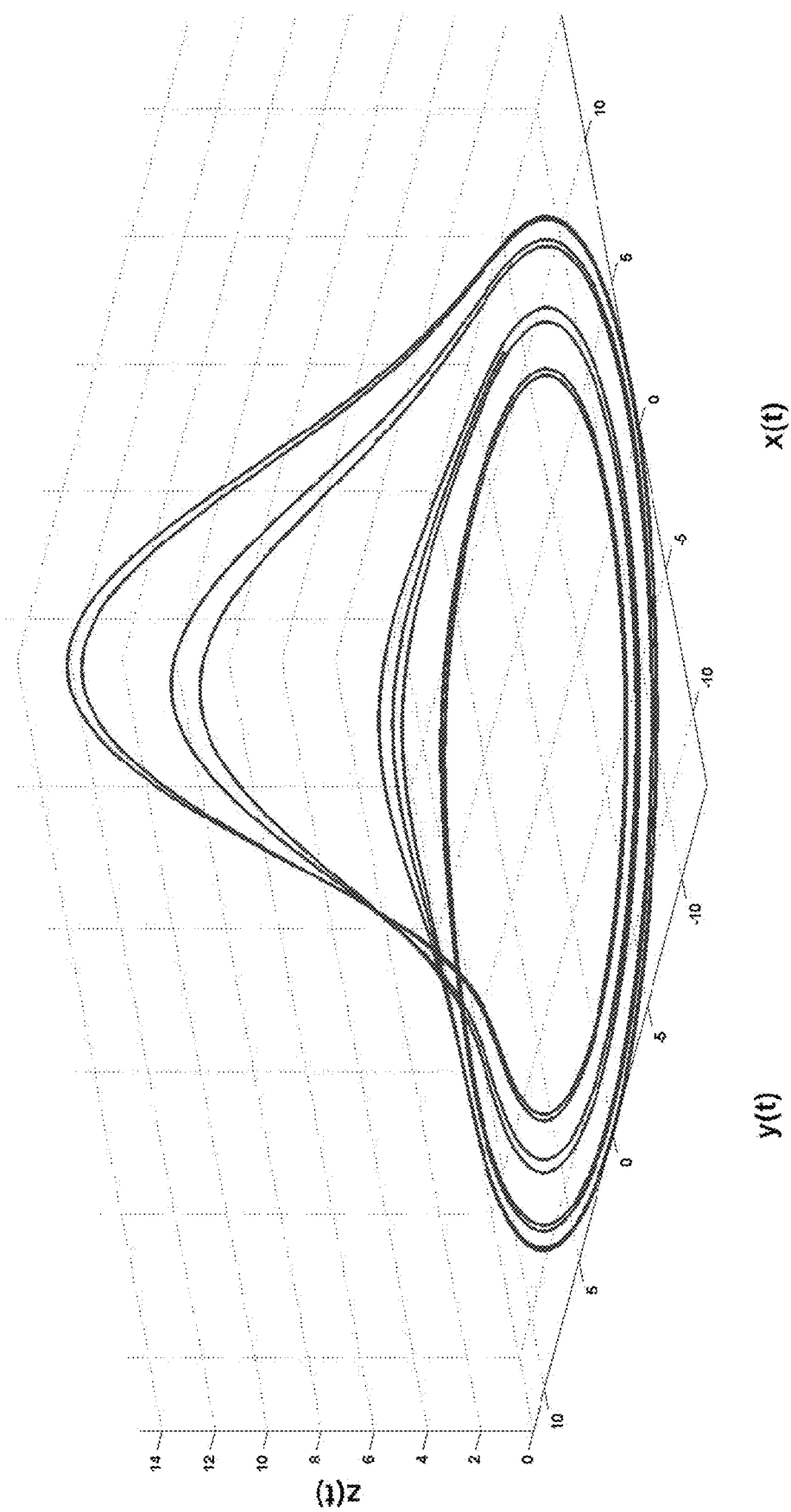
Figure 9E:
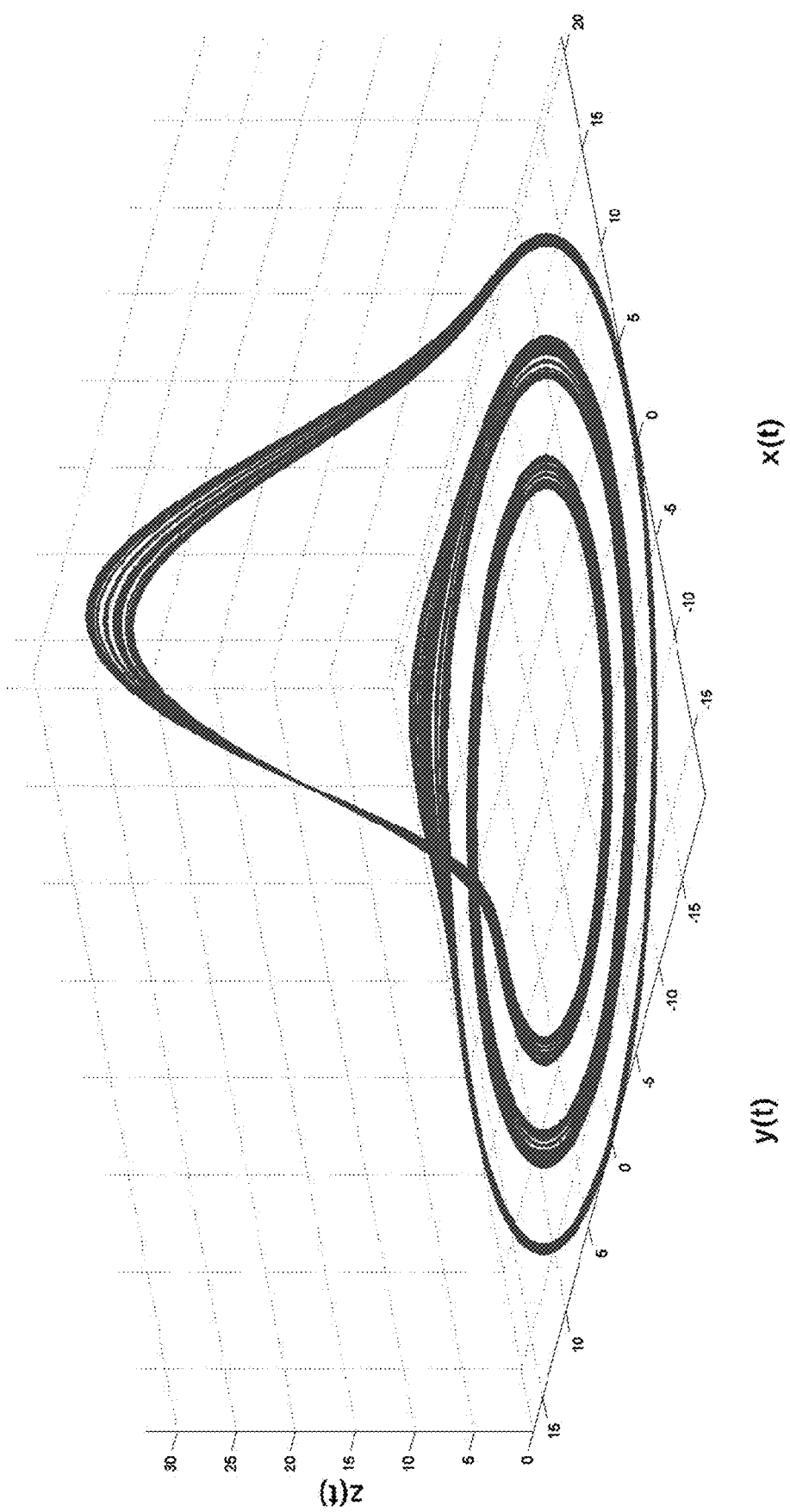
Figure 9F:
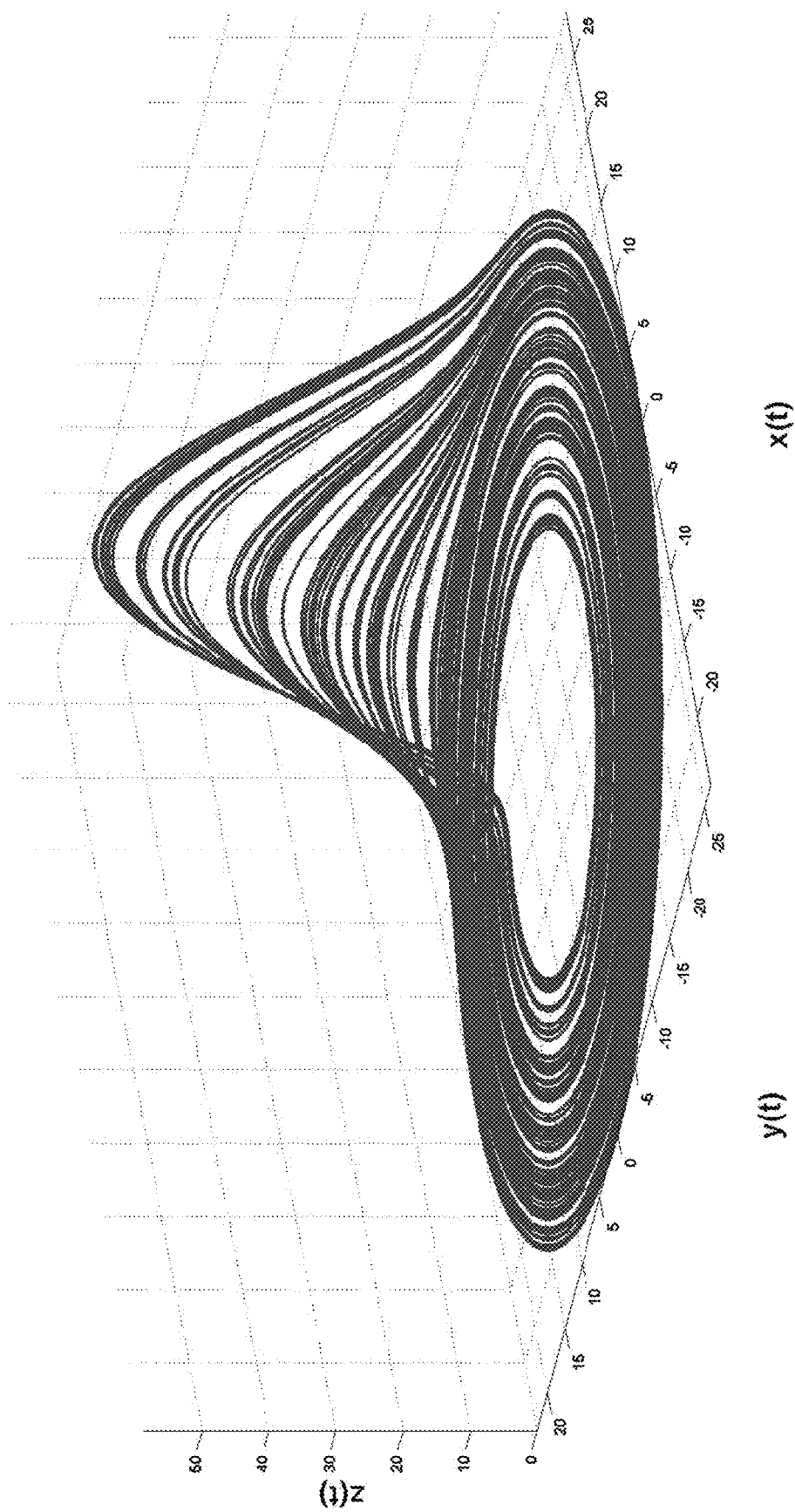
Figure 10A:
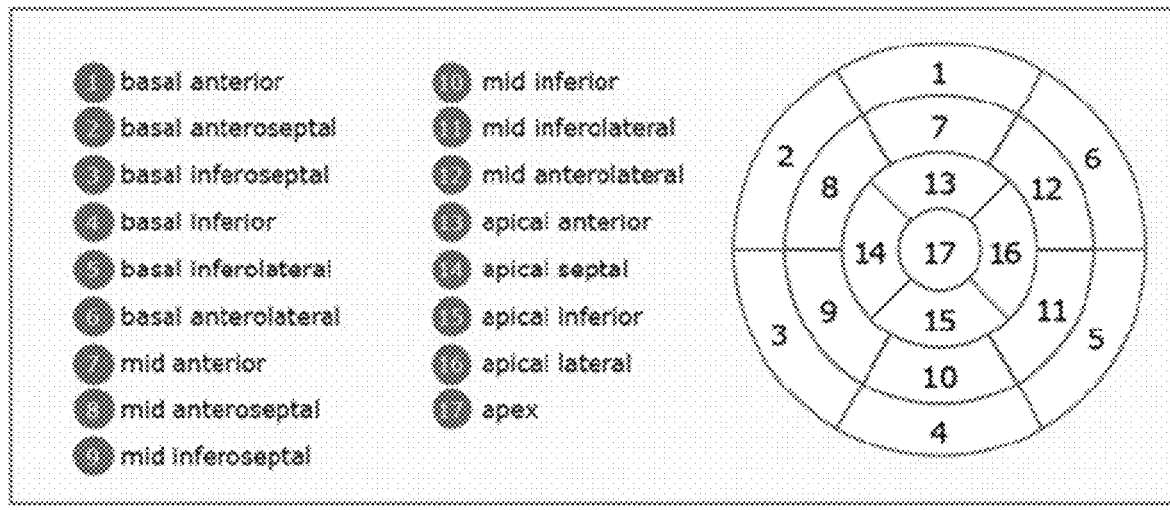
FIGS. 10A and 10B illustrate definitions of regions of the heart.
Figure 10B:
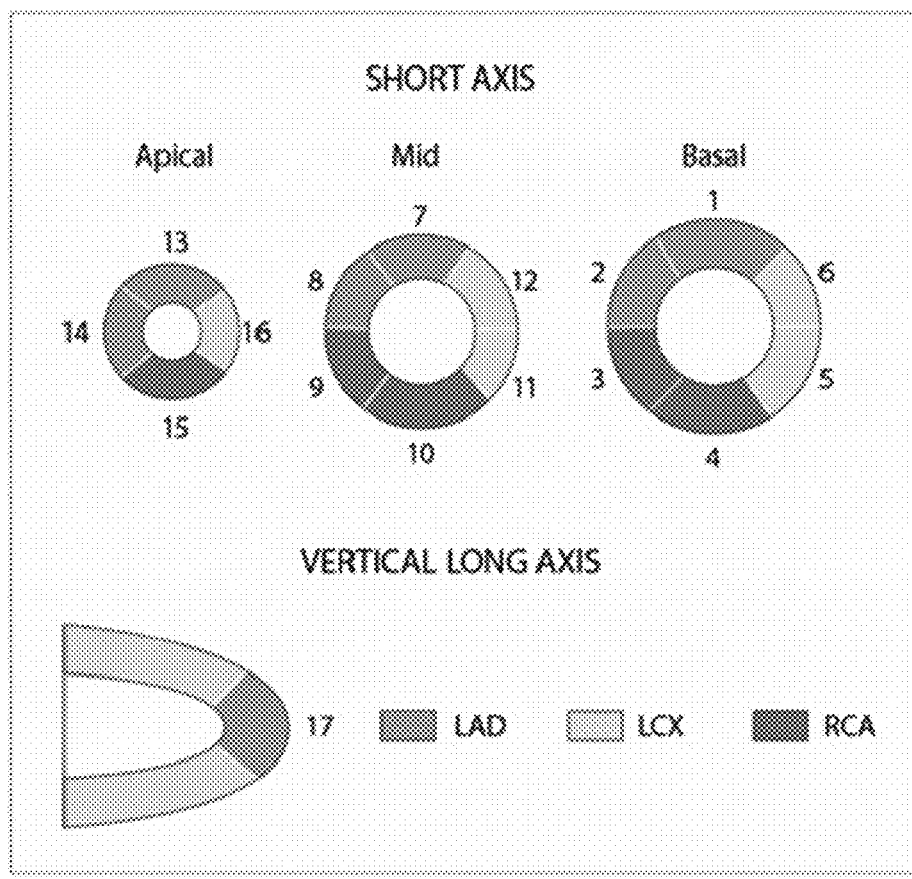

Examples of the 3-D phase space plot are shown in FIGS. 8-10. FIG. 8A shows a 3-D model of a heart where abnormal electrical/anatomical features are highlighted in red. FIG. 8B is the representation of this data using a 17-segment cardiac anatomical map in common use (see FIGS. 10A and 10B). FIGS. 9A-9F present different dynamical behaviors of Rossler system for different values of its parameter, c. FIGS. 10A and 10B illustrate definitions of regions of the heart.

The 3-D phase space plot of the present disclosure may be displayed by any type of computing device, including, but not limited to, desktop computers, workstation computers, server computers, cloud computing devices, tablet devices, smart phones, and mobile computing devices.

Figure 11:
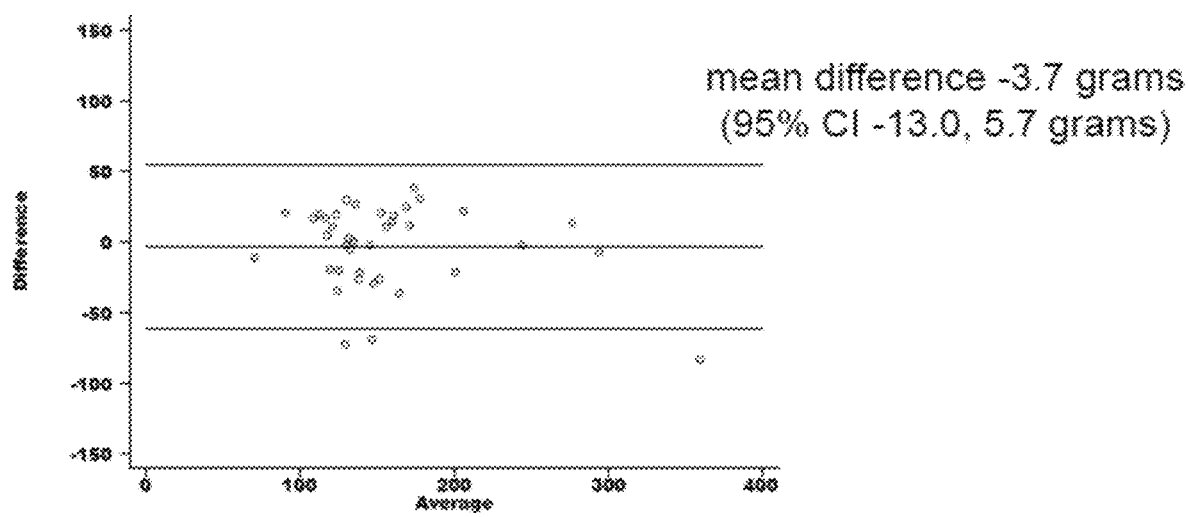
FIG. 11 demonstrates the ability of the disclosed methods to quantify left ventricular mass from only a high resolution ECG signal. This Bland-Altman plot indicates that the quantification of left ventricular mass by ECG using the methods disclosed is comparable to that of cardiac magnetic resonance (CMR) imaging, with clinically acceptable accuracy.
Figure 12:
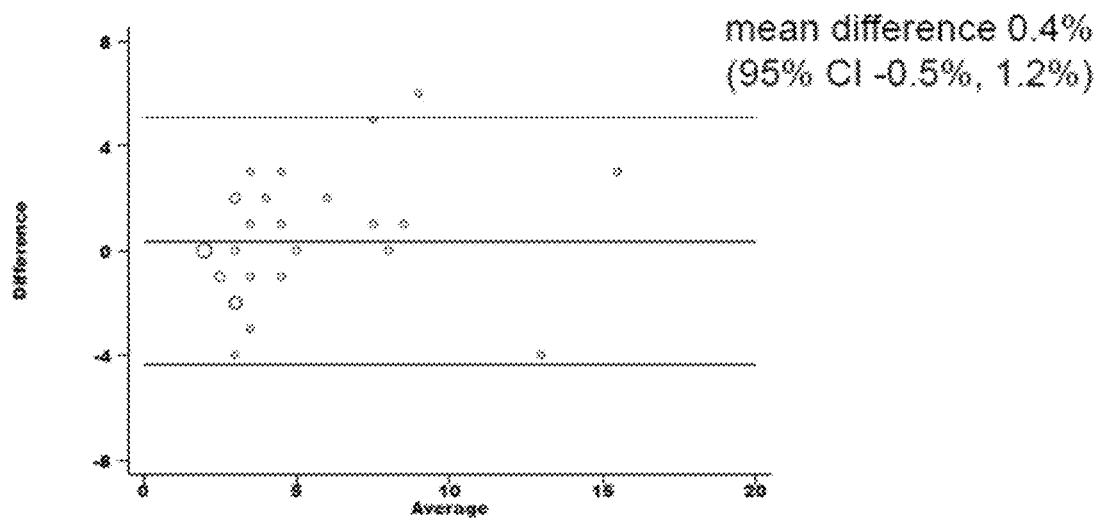
FIG. 12 demonstrates the ability of the disclosed methods to quantify left ventricular fibrosis from only a high resolution ECG signal. This Bland-Altman plot indicates that the quantification of left ventricular fibrosis by ECG using the methods disclosed is comparable to that of CMR late gadolinium enhancement (LGE) imaging, with clinically acceptable accuracy.

A methodology will now be described below for producing output from an algorithm that correlates with clinical parameters describing tissue architecture, structure and function. Descriptive attributes in that class include left ventricular mass and fibrosis as measured using CMR LGE imaging. As indicated in FIGS. 11 and 12, cardiac mass and fibrosis can be reliably detected and quantified using the implementations of the present disclosure. For example, the anatomic location of these changes can also be reliably determined using the disclosed methods, as shown by the data in FIG. 13.

FIG. 11 provides data related to the blind performance of the preceding formula for predicting left ventricular mass from just a high resolution ECG signal, compared to CMR, a method for assessing left ventricular mass. These data indicate that the methods disclosed provide a left ventricular mass value that is sufficiently close to the actual CMR value, to support the use of ECG data analyzed using the methods disclosed alone to quantify cardiac mass.

FIG. 12 provides data related to the blind performance of the preceding formula for predicting fibrosis from just a high resolution ECG signal, compared to CMR, a method for assessing fibrosis, assessed as percent LGE. These data indicate that the methods disclosed provide an estimate of fibrosis that is sufficiently close to the actual CMR value, to support the use of ECG data analyzed using the methods disclosed alone to estimate the percent of cardiac fibrosis.

The algorithm utilizes space-time densities computed using the space-time analysis method to create a predominantly time agnostic feature set representative of the dynamics of the signal propagation through tissue. The space-time metrics are then linked with clinical data sets, for example left ventricular mass, using a genetic learning algorithm. The subsequent result can then be used in independent data sets to reliably characterize the tissues of interest as shown in FIGS. 11, 12 and 13. Exemplar formulas for the clinical parameters related to these specific examples follow. It is explicitly noted that the formulas below are being provided solely as examples, and should not be construed as limiting the disclosure, as recited in the claims, as variations, modifications, and adaptations of the equations below to achieve the functions of the present disclosure are considered to be within the scope of the appended claims.

EXAMPLE FORMULAS

Estimate of percent fibrosis as measured using CMR LGE imaging=((cosh((gauss((SD1-SD2)))))/((gauss((gauss((SD3/(SD4*SD5))))))*(gauss((cosh((gauss((SD6+(SD12/(SD6*SD5))))))))))+(((gauss((gauss(SD7))))/((SD8*SD7)+(gauss(((gauss(SD9))+(gauss((((SD10*SD8)+((SD3^2)*SD7*(gauss(SD11))))/(SD1*SD2))))))))+(SD3+SD4+(SD6*(gauss((SD2*SD4))))+SD5*(gauss(((SD7*SD3)/((SD2*SD6)-(SD3*SD6))))))/SD3)+(gauss((SD1-(SD3*SD8))))+(gauss(((SD7*SD3)/((SD2*SD6)-(SD3*SD6))))-((cosh((gauss((SD1-SD2)))))/((gauss((gauss((SD3/(SD4*SD5))))))*(gauss((cosh((gauss((SD6+(SD12/(SD6*SD5))))))))))-((gauss((gauss(SD7))))/((SD8*SD7)+(gauss(((gauss(SD9))+(gauss((((SD10*SD8)+((SD3^2)*SD7*(gauss(SD11))))/(SD1*SD2))))))))*gauss(((SD3+SD4+(SD6*(gauss((SD2*SD4))))+((SD5*(gauss(((SD7*SD3)/((SD2*SD6)-(SD3*SD6))))))/SD3)+(gauss((SD1-(SD3*SD8))))+(gauss(((SD7*SD3)/((SD2*SD6)-(SD3*SD6))))^2+((cosh((gauss((SD1-SD2)))))/((gauss((gauss((SD3/(SD4*SD5))))))*(gauss((cosh((gauss((SD6+(SD12/(SD6*SD5))))))))))^2-((gauss((gauss(SD7))))/((SD8*SD7)+(gauss(((gauss(SD9))+(gauss((((SD10*SD8)+((SD3^2)*SD7*(gauss(SD11))))/(SD1*SD2))))))^2/((gauss((gauss(SD7))))/((SD8*SD7)+(gauss(((gauss(SD9))+(gauss((((SD10*SD8)+((SD3^2)*SD7*(gauss(SD11))))/(SD1*SD2))))))))+(SD3+SD4+(SD6*(gauss((SD2*SD4))))+OD5*(gauss(((SD7*SD3)/((SD2*SD6)-(SD3*SD6))))))/SD3)+(gauss((SD1-(SD3*SD8))))+(gauss(((SD7*SD3)/((SD2*SD6)-(SD3*SD6))))+((cosh((gauss((SD1-SD2)))))/((gauss((gauss((SD3/(SD4*SD5))))))*(gauss((cosh((gauss((SD6+(SD12/(SD6*SD5))))))))))+(SD3+SD4+(SD6*(gauss((SD2*SD4))))+((SD5*(gauss(((SD7*SD3)/((SD2*SD6)-(SD3*SD6))))))/SD3)+(gauss((SD1-(SD3*SD8))))+(gauss(((SD7*SD3)/((SD2*SD6)-(SD3*SD6))))^2+((cosh((gauss((SD1-SD2)))))/((gauss((gauss((SD3/(SD4*SD5))))))*(gauss((cosh((gauss((SD6+(SD12/(SD6*SD5))))))))^2))/cosh(((gauss((gauss(SD7))))/((SD8*SD7)+(gauss(((gauss(SD9))+(gauss((((SD10*SD8)+((SD3^2)*SD7*(gauss(SD11))))/(SD1*SD2))))))))^2/((SD3+SD4+(SD6*(gauss((SD2*SD4))))+OD5*(gauss(((SD7*SD3)/((SD2*SD6)-(SD3*SD6))))))/SD3)+(gauss((SD1-(SD3*SD8))))+(gauss(((SD7*SD3)/((SD2*SD6)-(SD3*SD6))))))*((cosh((gauss((SD1-SD2)))))/((gauss((gauss((SD3/(SD4*SD5))))))*(gauss((cosh((gauss((SD6+(SD12/(SD6*SD5))))))))))*gauss(((cosh((gauss((SD1-SD2)))))/((gauss((gauss((SD3/(SD4*SD5))))))*(gauss((cosh((gauss((SD6+(SD12/(SD6*SD5))))))))))^3*gauss(((gauss((gauss(SD7))))/((SD8*SD7)+(gauss(((gauss(SD9))+(gauss((((SD10*SD8)+((SD3^2)*SD7*(gauss(SD11))))/(SD1*SD2))))))))+(SD3+SD4+SD6*(gauss((SD2*SD4))))+((SD5*(gauss(((SD7*SD3)/((SD2*SD6)-(SD3*SD6))))))/SD3)+(gauss((SD1-(SD3*SD8))))+(gauss(((SD7*SD3)/((SD2*SD6)-(SD3*SD6))))+((cosh((gauss((SD1-SD2)))))/((gauss((gauss((SD3/(SD4*SD5))))))*(gauss((cosh((gauss((SD6+(SD12/(SD6*SD5))))))))))/((gauss((gauss(SD7))))/((SD8*SD7)+(gauss(((gauss(SD9))+(gauss((((SD10*SD8)+((SD3^2)*SD7*(gauss(SD11))))/(SD1*SD2))))))))-((cosh((gauss((SD1-D2))))/((gauss((gauss((SD3/(SD4*SD5))))))*(gauss((cosh((gauss((SD6+(SD12/(SD6*SD5))))))))))

SD=signal density

Estimation of left ventricular mass as measured using CMR=((SD9+(SD4*(cosh(SD5))))/((gauss(SD5))+(gauss(((SD1*SD10*SD7)/(((SD1*SD9*SD10*SD11*SD4)-SD11)-(SD9*SD10*SD12*SD7))-((SD1^2)*SD10*SD5)))))+((((SD4+(SD1*SD2)+(SD5*SD3)+(SD1*SD2*SD5))-SD8)/(cosh(((gauss((SD2+(SD4/SD1))))-(cosh((gauss((gauss(((SD1*SD3)+((-SD3)/SD5))))))*(SD2+(SD1*SD2)+(SD3/(SD2+(SD8*SD3*(gauss(((SD2^2)/SD6))))+(gauss(SD5))+(gauss((SD1/SD4))))))*((cosh(SD6)+(cosh((gauss((cosh(SD7))))+(cosh((((cosh((gauss(SD6))))^2+((cosh((gauss(SD6))))*(cosh((gauss((gauss((gauss(SD6))))))))+(cosh((gauss(SD9))))))-((SD9+(SD3*(cosh(SD5)))))/((gauss(SD5))+(gauss(((SD1*SD10*SD7)/(((SD1*SD9*SD10*SD11*SD4)-SD11)-(SD9*SD10*SD12*SD7))-((SD1^2)*SD10*SD5)))))^2*(((SD3+(SD1*SD2)+(SD5*SD3)+(SD1*SD2*SD5))-SD8)/(cosh(((gauss((SD2+(SD4/SD1))))-(cosh((gauss(((SD1*SD3)+((-SD3)/SD5))))))))/((SD2+(SD1*SD2)+(SD3/(SD2+(SD8*SD3*(gauss(((SD2^2)/SD6))))+(gauss(SD5))+(gauss((SD1/SD4))))))^2+(SD2+(SD1*SD2)+(SD3/(SD2+(SD8*SD3*(gauss(((SD2^2)/SD6))))+(gauss(SD5))+(gauss((SD1/SD4))))))^3*gauss((((SD3+(SD1*SD2)+(SD5*SD3)+(SD1*SD2*SD5))-SD8)/(cosh(((gauss((SD2+(SD4/SD1))))-(cosh((gauss(((SD1*SD3)+((-SD3)/SD5))))))))*((SD2+(SD1*SD2)+(SD3/(SD2+(SD8*SD3*(gauss(((SD2^2)/SD6))))+(gauss(SD5))+(gauss((SD1/SD4))))))))/(((SD9+(SD3*(cosh(SD5))))/((gauss(SD5))+(gauss(((SD1*SD10*SD7)/(((SD1*SD9*SD10*SD11*SD4)-SD11)-(SD9*SD10*SD12*SD7))-((SD1^2)*SD10*SD5))))^2)))

SD=signal density

Ischemia of cardiac tissues is linked to the development of physiological changes that could alter complex sub-harmonics and results in variable and high dimensional changes. FIG. 7 illustrates one embodiment of a method whereby MMP is used to generate a 3-D vectorgram to localize, image, and characterize aberrant architectural features of the myocardium based on CSF identification, quantification and localization.

In accordance with the present disclosure, physiological and pathophysiological features of tissues are modeled accurately and effectively using fractional derivatives. In contrast, classical integer derivative-based models capture these phenomena only approximately or not at all. Traditional integer order derivatives depend only on the local behavior of a function, while fractional derivatives depend on the whole history of the function. In this embodiment, there is utilized a method for detecting beat to beat complex subharmonic structures in the ECG based on digital differentiation and integration of fractional order. Since these signals are mathematically modeled as a linear combination of the selected atoms, they can be differentiated and integrated of fractional order. Let x' (t), y' (t), and z' (t) be their integer order derivatives respectively, these derivatives and there ratios measure instability only at a local point of the signal and therefore are poor measures of stability for long complex ECG signals with significant beat-to-beat variability. An alternative to an integer derivative is the use of a fractional calculus to detect abnormal CSF signals in a physiological signal based on its past history.

There are two concepts regarding the low-energy component subspace (made from the last 20% terms found by MMP) that are interesting and useful. First, the fractional derivative of this component can be noiselessly obtained, since it is a linear combination of selected atoms, and this fractional derivative can be useful to localize, image, and characterize architectural features of tissues. In addition, there are some useful fractional properties to consider. Thus suppose that x(t),y(t), and z(t) are respectively the X, Y, and Z coordinates of the low-energy component and let $x^\alpha(t)$, $y^\alpha(t)$, and $z^\alpha(t)$ be their irrational fractional derivative of order $\alpha$ that can be any real(or complex) number. Then the magnitude of these irrational fractional derivatives can indicate instability when large and positive. Consider the regions when the irrational fractional derivatives are positive, in such regions, the low energy re-entrant wavelets that signify alterations in tissue architecture and, or function.

The phase space plot information cannot be easily superimposed on a 3-D representation of a given tissue since physiological function is variable across individuals. To overcome this problem, intrinsic phase space imaging does not use the interference in the phase plane of interest. Noiseless subspaces allow the recording of the phase of these waves. In cardiac tissues the amplitude resulting from this interference can be measured, however the phase of the orthogonal leads still carries the information about the structure and generates geometrical contrast in the image, thus the name phase-contrast imaging.

In phase-based imaging, phase-contrast takes advantage of the fact that different bioelectric structures have different impedances, and so spectral and non-spectral conduction delays and bend the trajectory of phase space orbit through the heart by different amounts. These small changes in trajectory can be normalized and quantified on a beat-to-beat basis and corrected for lead placement and the normalized phase space integrals can be mapped to a geometric mesh using a genetic algorithm to map 17 myocardial segments in the ventricle to various tomographic imaging modalities of the heart from retrospective data (exemplar formulas for 3 of the 17 regions below). FIG. 13 provides data related to the blind performance of localizing tissue abnormalities from just a high resolution ECG signal, compared to CMR, an accurate localization method. These data indicate that the methods disclosed provide a reliable means to localize the anatomic location of the tissue alteration. Thus, the disclosed method can be used to assess the effects (positive and negative) of various interventions that alter cardiovascular tissue architecture and, or function including medications, toxins, chemotherapeutic agents, surgical procedures, and other interventional procedures such as ablation, pacing, shocks and electrical therapies, and genetic therapies.

basal anterior segment=cosh(SD10)−gauss(SD11*SD12*SDCSF1+
0.005778*SDCSF2*SD6*SD10*SDCSF3−
6.749*SDCSF4*(gauss((((0.0735+(0.3203*SDCSF5*
(gauss((30.33*SD8*(gauss(((SD8+
((61.1*SDCSF6*SDCSF7)/((SDCSF8*(gauss
((9.666*SD1*SDCSF9*SDCSF10))))+(SDCSF11*
(gauss((9.666*SD1*SDCSF9*SDCSF10))))+
(SDCSF8*SDCSF12*SDCSF6*SDCSF7*(gauss
((9.666*SD1*SDCSF9*SDCSF10))))))))−(gauss
((gauss(SDCSF7))))))))))))−(2.994*SD10))−(17.03*
(gauss((6.882*(gauss(((SD8+
((61.1*SDCSF6*SDCSF7)/((SDCSF8*(gauss
((9.666*SD1*SDCSF9*SDCSF10))))+(SDCSF11*
(gauss((9.666*SD1*SDCSF9*SDCSF10))))+
(SDCSF8*SDCSF12*SDCSF6*SDCSF7*(gauss
((9.666*SD1*SDCSF9*SDCSF10))))))))−(gauss
((gauss(SDCSF7))))))))))))/SD1)))*gauss(SD1))
mid inferolateral segment=gauss(7.44069511*SD1+
6*SD1*SD2+−2.51202217109399*SD3/SD4+
SD5*SD6/(SD7*SD8)−SD3*SD8*SD9−
0.8372177305*SD1*SD4)
apical inferior segment=gauss((SD2*SD3−0.2868*SD3−
0.2308*gauss(14.35*SD2−9.859*SD4)/(SD1^2*
((0.8889*((((gauss((((SD3/(SD1+(SD1*SD5)))+
(1.764e−6*SD1*(SD5^2)*(SD6/SD7))+(SD5*((−
1*SD1)^2)*(SD6/(SD5*SD7))))−(SD1*SD3))))*
(gauss((SD8^2))))+(((gauss((SDCSF4/(gauss(((SD9+
SDCSF10)−1.959))))))*(gauss((SD10*(gauss
(SDCSF12))*((gauss((((SDCSF10+(13.62*(gauss
(SDCSF12))))−1.365)/SDCSF4)))/SDCSF2))))*(gauss
(((SD1−(gauss((((SD3/(SD1+(SD1*SD5)))+(1.764e−
6*SD1*(SD5^2)*(SD6/SD7))+(SD5*((−1*SD1)^2)*
(SD6/(SD5*SD7))))−(SD1*SD3))))/(SD6*(gauss
((SD8^2))))))))/(gauss(SD8)))+(0.8999*(gauss
((((((SDCSF8+SD11)−12.05)−
(SD1*SD12*SDCSF1))−(12.93*SD1*SD12))/(−
5.393−SD5))))))/1.8))+((SD1*((((gauss((((SD3/(SD1+
(SD1*SD5)))+(1.764e−6*SD1*(SD5^2)*(SD6/SD7))+
(SD5*((−1*SD1)^2)*(SD6/(SD5*SD7))))−
(SD1*SD3))))*(gauss((SD8^2))))+(((gauss((SDCSF4/
(gauss(((SD9+SDCSF10)−1.959))))))*(gauss((SD10*
(gauss(SDCSF12))*((gauss((((SDCSF10+(13.62*
(gauss(SDCSF12))))−1.365)/SDCSF4)))/SDCSF2))))*
(gauss(((SD1−(gauss((((SD3/(SD1+(SD1*SD5)))+
(1.764e−6*SD1*(SD5^2)*(SD6/SD7))+(SD5*((−
1*SD1)^2)*(SD6/(SD5*SD7))))−(SD1*SD3)))))/
(SD6*(gauss((SD8^2)))))))/(gauss(SD8)))+(0.899.9*
(gauss((((((SDCSF8+SD11)−12.05)−
(SD1*SD12*SDCSF1)−(12.93*SD1*SD12))/(−
5.393−SD5))))))/1.8))/SD8)+((35.21*SDCSF2*
((((gauss((((SD3/(SD1+(SD1*SD5)))+(1.764e−
6*SD1*(SD5^2)*(SD6/SD7))+(SD5*((−1*SD1)^2)*
(SD6/(SD5*SD7))))−(SD1*SD3))))*(gauss
((SD8^2))))+(((gauss((SDCSF4/(gauss(((SD9+
SDCSF10)−1.959))))))*(gauss((SD10*(gauss
(SDCSF12))*((gauss((((SDCSF10+(13.62*(gauss
(SDCSF12))))−1.365)/SDCSF4)))/SDCSF2))))*(gauss
(((SD1−(gauss((((SD3/(SD1+(SD1*SD5)))+(1.764e−
6*SD1*(SD5^2)*(SD6/SD7))+(SD5*((−1*SD1)^2)*
(SD6/(SD5*SD7))))−(SD1*SD3))))/(SD6*(gauss
((SD8^2))))))))/(gauss(SD8)))+(0.8999*(gauss
((((((SDCSF8+SD11)−12.05)−
(SD1*SD12*SDCSF1))−(12.93*SD1*SD12))/(−
5.393−SD5))))))/1.8))/SD5)+((−5997000*SDCSF3*
((((gauss((((SD3/(SD1+(SD1*SD5)))+(1.764e−
6*SD1*(SD5^2)*(SD6/SD7))+(SD5*((−1*SD1)^2)*

(SD6/(SD5*SD7))))−(SD1*SD3))))*(gauss
((SD8^2))))+(((gauss((SDCSF4/(gauss(((SD9+
SDCSF10)−1.959))))))*(gauss((SD10*(gauss
(SDCSF12))*((gauss((((SDCSF10+(13.62*(gauss
(SDCSF12))))−1.365)/SDCSF4)))/SDCSF2))))*(gauss
(((SD1−(gauss((((SD3/(SD1+(SD1*SD5)))+(1.764e−
6*SD1*(SD5^2)*(SD6/SD7))+(SD5*((−1*SD1)^2)*
(SD6/(SD5*SD7))))−(SD1*SD3)))))/(SD6*(gauss
((SD8^2))))))))/(gauss(SD8)))+(0.8999*(gauss
((((((SDCSF8+SD11)−12.05)−
(SD1*SD12*SDCSF1))−(12.93*SD1*SD12))/(−5.393
SD5))))))/1.8))/SD11))+((0.8889*((((gauss((((SD3/
(SD1+(SD1*SD5)))+(1.764e−6*SD1*(SD5^2)*(SD6/
SD7))+(SD5*((−1*SD1)^2)*(SD6/(SD5*SD7))))−
(SD1*SD3))))*(gauss((SD8^2))))+(((gauss((SDCSF4/
(gauss(((SD9+SDCSF10)−1.959))))))*(gauss((SD10*
(gauss(SDCSF12))*((gauss((((SDCSF10+(13.62*
(gauss(SDCSF12))))−1.365)/SDCSF4)))/SDCSF2))))*
(gauss(((SD1−(gauss((((SD3/(SD1+(SD1*SD5)))+
(1.764e−6*SD1*(SD5^2)*(SD6/SD7))+(SD5*((−
1*SD1)^2)*(SD6/(SD5*SD7))))−(SD1*SD3)))))/
(SD6*(gauss((SD8^2))))))))/(gauss(SD8)))+(0.899.9*
(gauss((((((SDCSF8+SD11)−12.05)−
(SD1*SD12*SDCSF1))−(12.93*SD1*SD12))/(−
5.393−SD5))))))/1.8))+*((((gauss((((SD3/(SD1+
(SD1*SD5)))+(1.764e−6*SD1*(SD5^2)*(SD6/SD7))+
(SD5*((−1*SD1)^2)*(SD6/(SD5*SD7))))−
(SD1*SD3))))*(gauss((SD8^2))))+(((gauss((SDCSF4/
(gauss(((SD9+SDCSF10)−1.959))))))*(gauss((SD10*
(gauss(SDCSF12))*((gauss((((SDCSF10+(13.62*
(gauss(SDCSF12))))−1.365)/SDCSF4)))/SDCSF2))))*
(gauss(((SD1−(gauss((((SD3/(SD1+(SD1*SD5)))+
(1.764e−6*SD1*(SD5^2)*(SD6/SD7))+(SD5*((−
1*SD1)^2)*(SD6/(SD5*SD7))))−(SD1*SD3)))))/
(SD6*(gauss((SD8^2))))))))/(gauss(SD8)))+(0.8999*
(gauss((((((SDCSF8+SD11)−12.05)−
(SD1*SD12*SDCSF1))−(12.93*SD1*SD12))/(−5.393
SD5))))))/1.8))/SD8)+((35.21*SDCSF2*((((gauss
((((SD3/(SD1+(SD1*SD5)))+(1.764e−6*SD1*
(SD5^2)*(SD6/SD7))+(SD5*((−1*SD1)^2)*(SD6/
(SD5*SD7))))−(SD1*SD3))))*(gauss((SD8^2))))+
(((gauss((SDCSF4/(gauss(((SD9+SDCSF10)−
1.959))))))*(gauss((SD10*(gauss(SDCSF12))*((gauss
((((SDCSF10+(13.62*(gauss(SDCSF12))))−1.365)/
SDCSF4)))/SDCSF2))))*(gauss(SD1−(gauss((((SD3/
(SD1+(SD1*SD5)))+(1.764e−6*SD1*(SD5^2)*(SD6/
SD7))+(SD5*((−1*SD1)^2)*(SD6/(SD5*SD7))))−
(SD1*SD3)))))/(SD6*(gauss((SD8^2))))))))/(gauss
(SD8)))+(0.8999*(gauss((((((SDCSF8+SD11)−
12.05)−(SD1*SD12*SDCSF1))−(12.93*SD1*SD12))/
(−5.393 SD5))))))/1.8))/SD5)+((−5997000*SDCSF3*
((((gauss((((SD3/(SD1+(SD1*SD5)))+(1.764e−
6*SD1*(SD5^2)*(506/507))+(SD5*((−1*SD1)^2)*
(SD6/(SD5*SD7))))−(SD1*SD3))))*(gauss
((SD8^2))))+(((gauss((SDCSF4/(gauss(((SD9+
SDCSF10)−1.959))))))*(gauss((SD10*(gauss
(SDCSF12))*((gauss(SDCSF10+(13.62*(gauss
(SDCSF12))))−1.365)/SDCSF4)))/SDCSF2))))*(gauss
(((SD1−(gauss((((SD3/(SD1+(SD1*SD5)))+(1.764e−
6*SD1*(SD5^2)*(SD6/SD7))+(SD5*((−1*SD1)^2)*
(SD6/(SD5*SD7))))−(SD1*SD3)))))/(SD6*(gauss
((SD8^2))))))))/(gauss(SD8)))+(0.899.9*(gauss
((((((SDCSF8+SD11)−12.05)−
(SD1*SD12*SDCSF1))−(12.93*SD1*SD12))/(−
5.393−SD5))))))/1.8))/SD11))^3))
SD=signal density SDCSF=signal density complex-sub-harmonic-frequencies In the second method, space-time domain is divided into a number of regions (for example, 12 regions for ventricular and 6 regions for atrial tissues); the density of the baseline-removed ECG signal is computed in each region. These values contain specific information about the non-linear variability of the physiological signal, specifically the ECG signal, that are linked to an alteration in tissue architecture and, or function. The calcium ion (Ca++) is a universal intracellular messenger. In muscle, Ca++ is central to contractile force activation. Ca++ is also important for temporal and spatial alterations in action potentials, modulation of contractile function due to systemic resistance (blood pressure), energy supply-demand balance (including mitochondrial function), cell death (apoptosis), and transcription regulation. It has been hypothesized that Ca++-dependent ion pump variability occurs aperiodically in pathological cardiac myocytes, this creates significant microvolt beat-to-beat variations in the ECG signals and possibly other physiological signals (e.g., arterial pulse waveform). Variations in the ECG or other physiological signal can be measured and localized by linking the space time density structures to tissues of interest (for example, the 12 ventricular and 6 atrial regions). It should be noted a simple derivative or its ratios is not sufficient to characterize space-time density structures over many cardiac cycles.

For the cardiac ventricle the 12 quantities are input to a genetic algorithm and are modeled to link 17 myocardial segments in the ventricle (see FIGS. 10A and 10B) to various tomographic imaging modalities of the heart (collected data). The region boundaries are agnostic to the physiological signal, for example the clinical ECG landmarks commonly referred to as P, Q, R, S, T, and U waves. The result is 17 nonlinear nested sinusoidal Gaussian equations for the ventricle that link the 12 dimensional space-time density metrics to tomographic imaging modalities of the collected data. These same ECG metrics can be used to localize, image, and characterize architectural features and function of tissues, in the example, the heart.

Ectopic foci can produce dynamic spatial dispersion of repolarization and conduction block, initiating re-entrant arrhythmias. Dynamic spatial dispersion of repolarization in atrial and ventricular tissues can be detected and localized using space-time analysis on the described 6 atrial and 12 ventricular 6 regions. These quantities are then inputted into a genetic algorithm and are modeled to link regions of interest to various tomographic images from collected data.

Spatial changes in the phase space matrix can be can be computed using non-Fourier or Fourier multi-dimensional fractional integral summation across all ECG leads on the derived model to generate the dynamical space-time density metrics. For cardiac ventricular tissue these metrics are modeled using a genetic algorithm to link 17 non-linear nested sinusoidal Gaussian equations previously described to the commonly used 17-segment model shown in FIGS. 10A and 10B. Segments with altered architectural features and, or function are identified and the degree of abnormality quantified, permitting assigning a probability of the said tissue having a pathophysiological abnormality that can be characterized as hypertrophy, atrophy, scar, ischemia, edema, fibrosis or another condition. For example, the probability of regional ischemia in a ventricular segment can be identified and quantified as shown in FIGS. 8A and 8B.

Having thus described several embodiments of the present disclosure, it will be rather apparent to those skilled in the art that the foregoing detailed disclosure is intended to be presented by way of example only, and is not limiting. Many advantages for non-invasive method and system for localization, imaging, and characterization of architectural features and function of tissues have been discussed herein. Various alterations, improvements, and modifications will occur and are intended to those skilled in the art, though not expressly stated herein. These alterations, improvements, and modifications are intended to be suggested hereby, and are within the spirit and the scope of the present disclosure. Additionally, the recited order of the processing elements or sequences, or the use of numbers, letters, or other designations therefore, is not intended to limit the claimed processes to any order except as may be specified in the claims. Accordingly, the present disclosure is limited only by the following claims and equivalents thereto.

What is claimed is:

1. A method of extracting variable for use in a machine learning operation to diagnose a pathology, the method comprising:
    receiving, via a processor, a biopotential signal data set associated with a subject, said biopotential signal data set being associated with a biopotential signal collected from one or more electrical leads;
    determining, via the processor, a plurality of parameters of dynamical features of the received biopotential signal data set for a dictionary that estimates a model of the received biopotential signal data set, wherein the plurality of dynamical features includes Lyapunov exponent and correlation dimension features; and
    linking, via the processor, the plurality of determined parameters of the dynamical features to a genetic algorithm for producing outputs that correlate with clinical parameters describing tissue architecture, structure and/or function.

2. The method of claim 1, wherein the model comprises a subspace selected from the group consisting of a CSF trajectory subspace of the received biopotential signal data set, a quasi-periodic and chaotic subspace of the received biopotential signal data set, and a low/high-energy subspace of the received biopotential signal data set.

3. The method of claim 1, wherein the biopotential signal data set comprises electrocardiographic signals.

4. The method of claim 1 further comprising:
    removing, by the processor, baseline wander from the received biopotential signal data set.

5. The method of claim 4, wherein the baseline wander is removed using a modified moving average filter.

6. The method of claim 1 comprising:
    detecting, by the processor, a disease or pathophysiological abnormality selected from the group consisting of hypertrophy, ischemia, scar, and abnormal electrical channel function.

7. The method of claim 1, wherein the outputs of the genetic algorithms are linked to a 17-myocardial segment model of the ventricle.

8. The method of claim 6 further comprising:
    identifying, by the processor, using the determined parameters of the dynamical features, segments of the 17-myocardial segment model with altered architectural features and/or function.

9. The method of claim 8, wherein one or more segments of the 17-myocardial segment model are assigned a probability value of a corresponding tissue having a pathophysiological abnormality.

10. A system to extract variable for use in machine learning operation to diagnose a pathology, the system comprising:
    a processor;
    a memory having instructions stored thereon, wherein execution of the instructions by the processor causes the processor to:
        receive a biopotential signal data set associated with a subject, said biopotential signal data set being associated with a biopotential signal collected from one or more electrical leads;
        determine a plurality of parameters of dynamical features of the received biopotential signal data set for a dictionary that estimates a model of the received biopotential signal data set, wherein the plurality of dynamical features includes Lyapunov exponent and correlation dimension; and
        link the plurality of determined parameters of the dynamical features to a genetic algorithm for producing outputs that correlate with clinical parameters describing tissue architecture, structure and/or function.

11. The system of claim 10, wherein the model comprises a subspace selected from the group consisting of a CSF trajectory subspace of the received biopotential signal data set, a quasi-periodic and chaotic subspace of the received biopotential signal data set, and a low/high-energy subspace of the received biopotential signal data set.

12. The system of claim 10, wherein the biopotential signal data set comprises electrocardiographic signals.

13. The system of claim 10, wherein execution of the instructions by the processor further causes the processor to remove baseline wander from the received biopotential signal data set.

14. The system of claim 13, wherein the baseline wander is removed using a modified moving average filter.

15. The system of claim 10, wherein execution of the instructions by the processor further causes the processor to detect a disease or pathophysiological abnormality selected from the group consisting of hypertrophy, ischemia, scar, and abnormal electrical channel function.

16. The system of claim 10, wherein the outputs of the genetic algorithms are linked a 17-myocardial segment model of the ventricle.

17. The system of claim 16, wherein execution of the instructions by the processor further causes the processor to identify segments of the 17-myocardial segment model with altered architectural features and/or function.

18. The system of claim 17, wherein one or more segments of the 17-myocardial segment model are assigned a probability of a corresponding tissue having a pathophysiological abnormality.

19. A non-transitory computer readable medium having instructions stored thereon, wherein execution of the instructions by a processor causes the processor to:
    receive a biopotential signal data set associated with a subject, said biopotential signal data set being associated with a biopotential signal collected from one or more electrical leads;
    determine a plurality of parameters of dynamical features of the received biopotential signal data set for a dictionary that estimates a model of the received biopotential signal data set, wherein the plurality of dynamical features includes Lyapunov exponent and correlation dimension features; and
    link the plurality of determined parameters of the dynamical features to a genetic algorithm for producing outputs that correlate with clinical parameters describing tissue architecture, structure and/or function.

20. The computer readable medium of claim 19, wherein the model comprises a subspace selected from the group consisting of a CSF trajectory subspace of the received biopotential signal data set, a quasi-periodic and chaotic subspace of the received biopotential signal data set, and a low/high-energy subspace of the received biopotential signal data set.

* * * * *